(12) United States Patent
Smith et al.

(10) Patent No.: US 7,179,244 B2
(45) Date of Patent: Feb. 20, 2007

(54) RESETTABLE SAFETY SHIELD FOR MEDICAL NEEDLES

(75) Inventors: Daniel K. Smith, Woods Cross, UT (US); Jeremy W. Snow, North Salt Lake, UT (US); F. Mark Ferguson, Salt Lake City, UT (US)

(73) Assignee: Specialized Health Products, Inc., Bountiful, UT (US)

( * ) Notice: Subject to any disclaimer, the term of this patent is extended or adjusted under 35 U.S.C. 154(b) by 87 days.

(21) Appl. No.: 10/721,526

(22) Filed: Nov. 25, 2003

(65) Prior Publication Data

US 2004/0078003 A1 Apr. 22, 2004

Related U.S. Application Data

(63) Continuation-in-part of application No. 10/409,819, filed on Apr. 8, 2003, now Pat. No. 6,796,962, which is a continuation-in-part of application No. 10/322,288, filed on Dec. 17, 2002, and a continuation-in-part of application No. 10/202,201, filed on Jul. 23, 2002, now Pat. No. 6,902,546, which is a continuation-in-part of application No. 09/809,357, filed on Mar. 15, 2001, now Pat. No. 6,595,955.

(60) Provisional application No. 60/424,655, filed on Nov. 7, 2002.

(51) Int. Cl.
*A61M 5/32* (2006.01)

(52) U.S. Cl. .................. 604/110; 604/162; 604/164.08

(58) Field of Classification Search ............... 604/110, 604/162, 171, 163, 174, 180, 192, 197, 198, 604/263, 164.04, 164.08, 164.01, 170.01, 604/170.02, 117, 164.06, 164.07; 600/562, 600/564–567; 128/919

See application file for complete search history.

(56) References Cited

U.S. PATENT DOCUMENTS

| | | | |
|---|---|---|---|
| 1,436,707 A | 11/1922 | Gaschke | |
| 4,332,323 A | 6/1982 | Reenstierna | 206/365 |
| 4,373,526 A | 2/1983 | Kling | 128/215 |
| 4,762,516 A | 8/1988 | Luther | 605/164 |
| 4,790,828 A | 12/1988 | Dombrowski | 604/198 |
| 4,804,371 A | 2/1989 | Vaillancourt | 604/198 |
| 4,826,490 A | 5/1989 | Byrne | 604/198 |
| 4,832,696 A | 5/1989 | Luther | 604/164 |
| 4,834,718 A | 5/1989 | McDonald | 604/195 |
| 4,846,811 A | 7/1989 | Vanderhoof | 604/263 |

(Continued)

FOREIGN PATENT DOCUMENTS

EP 0 702 972 B1 7/1995

(Continued)

*Primary Examiner*—Cris Rodriguez
(74) *Attorney, Agent, or Firm*—Paul S. Evans

(57) ABSTRACT

A medical needle shield apparatus is provided that includes a needle hub having an outer needle cannula extending therefrom. An inner needle is disposed for slidable movement with the outer needle cannula. At least one shield is extensible from a retracted position to an extended position to enclose a distal end of the inner needle. The shield includes a binding member disposed within the shield and defines binding surfaces that form an aperture configured for slidable receipt of the inner needle. The binding member includes a binding member reset surface aligned with a hub reset surface for engagement therewith to allow reuse of a shielded needle apparatus.

33 Claims, 42 Drawing Sheets

U.S. PATENT DOCUMENTS

| | | | |
|---|---|---|---|
| 4,917,669 A | 4/1990 | Bonaldo | 604/164 |
| 4,929,241 A | 5/1990 | Kulli | 604/263 |
| 4,931,048 A | 6/1990 | Lopez | 604/110 |
| 4,944,725 A | 7/1990 | McDonald | 604/164 |
| 4,950,252 A | 8/1990 | Luther | 604/198 |
| 4,952,207 A | 8/1990 | Lemieux | 604/164 |
| 4,964,854 A | 10/1990 | Luther | 604/166 |
| 4,978,344 A | 12/1990 | Dombrowski | 604/198 |
| 4,994,041 A | 2/1991 | Dombrowski | 604/164 |
| 5,007,901 A | 4/1991 | Shields | 604/110 |
| 5,049,136 A | 9/1991 | Johnson | 604/198 |
| 5,051,109 A | 9/1991 | Simon | 604/263 |
| 5,053,017 A | 10/1991 | Chamuel | 604/192 |
| 5,059,180 A | 10/1991 | McLees | 604/110 |
| 5,084,023 A | 1/1992 | Lemieux | 604/167 |
| 5,084,030 A | 1/1992 | Byrne | 604/198 |
| 5,085,648 A | 2/1992 | Purdy | 604/198 |
| 5,127,905 A | 7/1992 | Lemieux | 604/164 |
| 5,135,504 A | 8/1992 | McLees | 604/164 |
| 5,147,327 A | 9/1992 | Johnson | 604/198 |
| 5,171,229 A | 12/1992 | McNeil | 604/192 |
| 5,183,468 A | 2/1993 | McLees | 604/164 |
| 5,205,829 A | 4/1993 | Lituchy | 604/164 |
| 5,215,528 A | 6/1993 | Purdy | 604/164 |
| 5,300,045 A | 4/1994 | Plassche | 604/263 |
| 5,312,371 A | 5/1994 | Dombrowski | 604/198 |
| 5,322,517 A * | 6/1994 | Sircom et al. | 604/198 |
| 5,328,482 A | 7/1994 | Sircom | 604/164 |
| 5,334,158 A | 8/1994 | McLees | 604/110 |
| 5,342,310 A | 8/1994 | Ueyama | 604/110 |
| 5,344,408 A | 9/1994 | Partika | 604/192 |
| 5,348,544 A | 9/1994 | Sweeney | 604/192 |
| 5,411,486 A | 5/1995 | Zadini | 604/198 |
| 5,417,659 A | 5/1995 | Gaba | 604/164 |
| 5,419,766 A | 5/1995 | Chang | 604/110 |
| 5,423,766 A | 6/1995 | Di Cesare | 604/192 |
| 5,458,658 A | 10/1995 | Sircom | 604/192 |
| 5,478,313 A | 12/1995 | White | 604/110 |
| 5,487,733 A | 1/1996 | Caizza et al. | 604/110 |
| 5,531,704 A | 7/1996 | Knotek | 604/192 |
| 5,533,974 A | 7/1996 | Gaba | 604/164 |
| 5,538,508 A | 7/1996 | Steyn | 604/192 |
| 5,549,570 A | 8/1996 | Rogalsky | 604/198 |
| 5,558,651 A | 9/1996 | Crawford | 604/263 |
| 5,562,624 A | 10/1996 | Righi | 604/110 |
| 5,562,633 A | 10/1996 | Wozencroft | 604/171 |
| 5,582,597 A | 12/1996 | Brimhall et al. | 604/192 |
| 5,584,809 A | 12/1996 | Gaba | 604/164 |
| 5,584,810 A | 12/1996 | Brimhall | 604/110 |
| 5,584,818 A | 12/1996 | Morrison | 604/197 |
| 5,599,310 A | 2/1997 | Bogert | 604/164 |
| 5,601,532 A | 2/1997 | Gaba | 604/110 |
| 5,601,536 A | 2/1997 | Crawford | 604/263 |
| 5,611,781 A | 3/1997 | Sircom | 604/164 |
| 5,662,610 A | 9/1997 | Sircom | 604/164 |
| 5,683,365 A | 11/1997 | Brown | 604/110 |
| 5,697,907 A | 12/1997 | Gaba | 604/110 |
| 5,718,688 A | 2/1998 | Wozencroft | 604/164 |
| 5,725,504 A | 3/1998 | Collins | 604/165 |
| 5,749,856 A | 5/1998 | Zadini | 604/162 |
| 5,853,393 A | 12/1998 | Bogert | 604/165 |
| 5,879,337 A | 3/1999 | Kuracina | 604/192 |
| 5,882,337 A | 3/1999 | Bogert | 604/110 |
| 5,910,130 A | 6/1999 | Caizza et al. | 604/110 |
| 5,911,705 A | 6/1999 | Howell | 604/110 |
| 5,951,515 A | 9/1999 | Osterlind | 604/110 |
| 5,980,488 A | 11/1999 | Thorne | 604/110 |
| 6,001,080 A | 12/1999 | Kuracina | 604/171 |
| 6,004,294 A | 12/1999 | Brimhall | 604/164 |
| 6,117,108 A | 9/2000 | Woehr | 604/110 |
| 6,132,401 A | 10/2000 | Van Der Meyden | 604/195 |
| 6,193,694 B1 | 2/2001 | Bell | 604/192 |
| 6,203,527 B1 | 3/2001 | Zadini | 604/110 |
| 6,210,373 B1 | 4/2001 | Allmon | 604/192 |
| 6,221,047 B1 | 4/2001 | Green et al. | 604/164 |
| 6,280,419 B1 | 8/2001 | Vojtasek | 604/192 |
| 6,287,278 B1 | 9/2001 | Woehr et al. | 604/110 |
| 6,406,459 B1 | 6/2002 | Allmon | 604/192 |
| 6,443,927 B1 | 9/2002 | Cook | 604/110 |
| 6,443,929 B1 | 9/2002 | Kuracina et al. | 604/192 |
| 6,585,704 B2 | 7/2003 | Luther et al. | 604/263 |
| 6,616,630 B1 | 9/2003 | Woehr et al. | 604/110 |
| 6,623,458 B2 | 9/2003 | Woehr et al. | 604/192 |
| 6,629,959 B2 | 10/2003 | Kuracina et al. | 604/192 |
| 6,652,486 B2 | 11/2003 | Bialecki et al. | 604/110 |
| 6,682,510 B2 | 1/2004 | Niermann | 604/263 |
| 2002/0099339 A1 | 7/2002 | Niermann | 604/263 |
| 2002/0107483 A1 | 8/2002 | Cook | 604/164.01 |
| 2002/0177813 A1 | 11/2002 | Adams et al. | 604/164.07 |
| 2002/0177818 A1 | 11/2002 | Vaillancourt | 604/198 |
| 2003/0036731 A1 | 2/2003 | Wilkinson et al. | 604/198 |
| 2003/0100868 A1 * | 5/2003 | Ferguson et al. | 604/263 |
| 2003/0114797 A1 | 6/2003 | Vaillancourt et al. | 604/171 |
| 2003/0135157 A1 | 7/2003 | Saulenas et al. | 604/110 |
| 2003/0144627 A1 | 7/2003 | Woehr et al. | 604/110 |
| 2003/0195471 A1 | 10/2003 | Woehr et al. | 604/164.08 |
| 2003/0195479 A1 | 10/2003 | Kuracina et al. | 604/263 |
| 2003/0216687 A1 | 11/2003 | Hwang | 604/110 |
| 2004/0010227 A1 | 1/2004 | Riesenberger et al. | 604/110 |
| 2004/0049155 A1 | 3/2004 | Schramm | 604/110 |
| 2005/0096592 A1 * | 5/2005 | Carlyon et al. | 604/110 |

FOREIGN PATENT DOCUMENTS

| | | |
|---|---|---|
| EP | 0 750 915 A2 | 1/1997 |
| EP | 1 027 903 A1 | 8/2000 |
| EP | 1 110 571 A1 | 6/2001 |
| EP | 1 112 754 A1 | 7/2001 |
| EP | 1 374 772 A1 | 1/2004 |
| WO | WO 97/42989 | 11/1997 |
| WO | WO 01/10488 A1 | 2/2001 |
| WO | WO 01/56642 | 8/2001 |
| WO | WO 02/45786 A2 | 6/2002 |
| WO | WO 03/103757 A1 | 12/2003 |

* cited by examiner

RESETTABLE SAFETY SHIELD FOR MEDICAL NEEDLES

CROSS-REFERENCE TO RELATED APPLICATIONS

This patent application is a continuation-in-part of U.S. Utility patent application Ser. No. 10/409,819, filed in the U.S. Patent and Trademark Office on Apr. 8, 2003 by Ferguson et al. now U.S. Pat. No. 6,796,962, which is a continuation-in-part of U.S. Utility application Ser. No. 10/322,288, filed in the U.S. Patent and Trademark Office on Dec. 17, 2002 by Ferguson et al., which claims priority to U.S. Provisional Patent application Ser. No. 60/424,655, filed in the U.S. Patent and Trademark Office on Nov. 7, 2002 by Bagley et al., and U.S. Utility patent application Ser. No. 10/202,201, filed in the U.S. Patent and Trademark Office on Jul. 23, 2002 by Ferguson et al. now U.S. Pat. No. 6,902,546, which is a continuation-in-part of U.S. Utility patent application Ser. No. 09/809,357, filed in the U.S. Patent and Trademark Office on Mar. 15, 2001 by Ferguson et al. now U.S. Pat. No. 6,595,955, the entire contents of each of these disclosures being hereby incorporated by reference herein.

BACKGROUND

1. Technical Field

The present disclosure generally relates to safety shields for medical needles, and more particularly, to resettable safety shields that protect a needle point of a medical needle.

2. Description of the Related Art

Problems associated with inadvertent needle sticks are well known in the art of blood sampling, percutaneous medication injection and other medical procedures involving use of medical needles. Significant attention has been focused on needle stick problems due to the contemporary sensitivity of exposure to AIDS, Hepatitis and other serious blood-borne pathogen exposures.

Procedures for removing a needle from a patient commonly require a technician to use one hand to place pressure at the wound site where the needle is being withdrawn, while removing the needle device with the other hand. It is also common practice for an attending technician to give higher priority to care for the patient than is given to disposal of a needle. In the case of typical needle devices without safety shields, such priority either requires the convenience of an available sharps container within reach or another means for safe disposal without leaving the patient's side. Providing adequate care while following safety procedures is often compounded by the patient's physical condition and mental state, such as in burn units and psychiatric wards. Under such conditions, it is difficult to properly dispose of a used needle while caring for a patient.

The widespread knowledge and history associated with needle care and disposal problems have resulted in numerous devices for preventing accidental needle sticks. Problems of current safety devices include difficulty of use and high cost due to their complexity and number of parts.

Other known devices employ sheaths that are spring activated, telescoping, pivoting, etc. These devices, however, may disadvantageously misfire or be cumbersome to activate. Further drawbacks of current devices include high manufacturing cost due to complexity and the number of parts. Thus, these type prior art devices may not adequately and reliably shield medical needle apparatus to prevent hazardous exposure.

Consequently, there remains a need to provide a more satisfactory solution for needle safety devices by overcoming the disadvantages and drawbacks of the prior art. Therefore, it would be desirable to provide a more adequate and reliable medical needle shield apparatus that employs a safety shield slidably movable along a medical needle to prevent hazardous exposure to a needle tip. It would be advantageous to provide such a safety shield that is capable of being reset to safely allow re-use of certain needle apparatus. Such a needle shield apparatus should be easily and reliably movable to shield a needle tip of a needle cannula.

SUMMARY

Accordingly, the present disclosure addresses a need for a medical needle shield apparatus which effectively and inexpensively protects a tip of a medical needle after use. The present disclosure resolves related disadvantages and drawbacks experienced in the art. More specifically, the apparatus and method of this invention constitute an important advance in the art of safety needle devices.

In one particular embodiment, a medical needle shield apparatus is provided in accordance with the principles of the present disclosure. The medical needle shield apparatus includes a needle hub having an outer needle cannula extending therefrom to a distal end. An inner needle is disposed for slidable movement with the outer needle cannula. At least one shield is extensible from a retracted position to an extended position to enclose a distal end of the inner needle. The shield includes a binding member disposed within the shield and defines binding surfaces that form an aperture configured for slidable receipt of the inner needle between the retracted position and the extended position.

The binding member includes at least one drag inducing member such that the member engages the inner needle during slidable receipt of the inner needle to create a drag force with the inner needle. The drag force facilitates rotation of the binding member relative to a longitudinal axis of the inner needle such that the binding surfaces engage the inner needle to prevent slidable movement of the inner needle in the extended position of the shield. The binding member further includes a needle communicating surface extending therefrom such that the needle communicating surface is engageable with the inner needle to prevent rotation of the binding member. A retainer extends transversely from the binding member for releasable engagement with the needle hub.

The binding member may be rotatable, relative to a longitudinal axis of the inner needle, between a non-binding orientation whereby the inner needle is slidable relative to the binding member and a binding orientation whereby the binding surfaces engage the inner needle to prevent slidable movement of the inner needle in the extended position of the at least one shield. The binding member may include one or more outwardly arcuate arms that extend to the needle-communicating surface.

The inner needle can be attached to a handle for manipulation thereof. The needle hub may define a hub slot configured for receipt of the retainer. The needle hub may be releasably mountable with a housing of the at least one shield. The medical needle shield apparatus may further include a plurality of shields.

The at least one drag inducing member may define a cavity that is substantially aligned with the aperture. The cavity is configured for slidable receipt of the needle to create the drag force with the needle. The binding member may include a substantially planar aperture plate that includes the binding surfaces that form the aperture. The at least one drag inducing member may include a pair of arms extending from the aperture plate. The arms can have curled end portions spaced apart from the aperture plate. The arms can include deflectable members.

The shield can include a housing that defines at least one blocking member extending from an interior surface thereof. The at least one blocking member can be engageable with the binding member for urging the binding member to a binding orientation. The aperture plate is axially movable for engagement with the at least one blocking member that causes rotation of the binding member to a binding orientation.

A binding member reset surface extends transversely from the binding member. The needle hub includes a hub reset surface aligned to contact with the binding member reset surface of an activated binding member when the shield housing is brought to mate concentrically with the needle hub. The hub reset surface deflects the binding member reset surface along with the needle engagement surface to a position above the inner needle surface and urges the binding member from the binding orientation to the sliding orientation. Concurrently, due to contact between the hub reset surface and binding member reset surface, the hub retainer is urged into a position that reengages the needle hub and retains the needle hub to the needle shield. In an illustrative embodiment, the hub reset surface is the distal facing surface of the hub retainer.

The medical needle shield apparatus may further be supported for relative rotational movement by at least one bearing.

In an alternate embodiment, the medical needle shield apparatus includes a shield being extensible from a retracted position to an extended position to enclose a distal end of the outer needle cannula. The shield defines a probe guide at a distal end thereof that is configured for receipt of a probe. The probe is configured for slidable movement with the outer needle cannula.

In another embodiment, the medical needle shield apparatus includes a needle hub having an outer needle cannula extending therefrom to a distal end. An inner needle is disposed for slidable movement with the outer needle cannula. A handle is attached to the inner needle and defines a flash chamber in communication with the inner needle. The flash chamber has a fitting, such as a luer connection, that facilitates connection to a medical device. A shield is releasably mountable to the needle hub and extensible from a retracted position to an extended position to enclose a distal end of the inner needle. The handle is disposed adjacent the shield.

BRIEF DESCRIPTION OF THE DRAWINGS

The foregoing and other features and advantages of the present invention will be more fully understood from the following detailed description of the exemplary embodiments, taken in conjunction with the accompanying drawings in which.

DETAILED DESCRIPTION OF THE EXEMPLARY EMBODIMENTS

Figure 1:
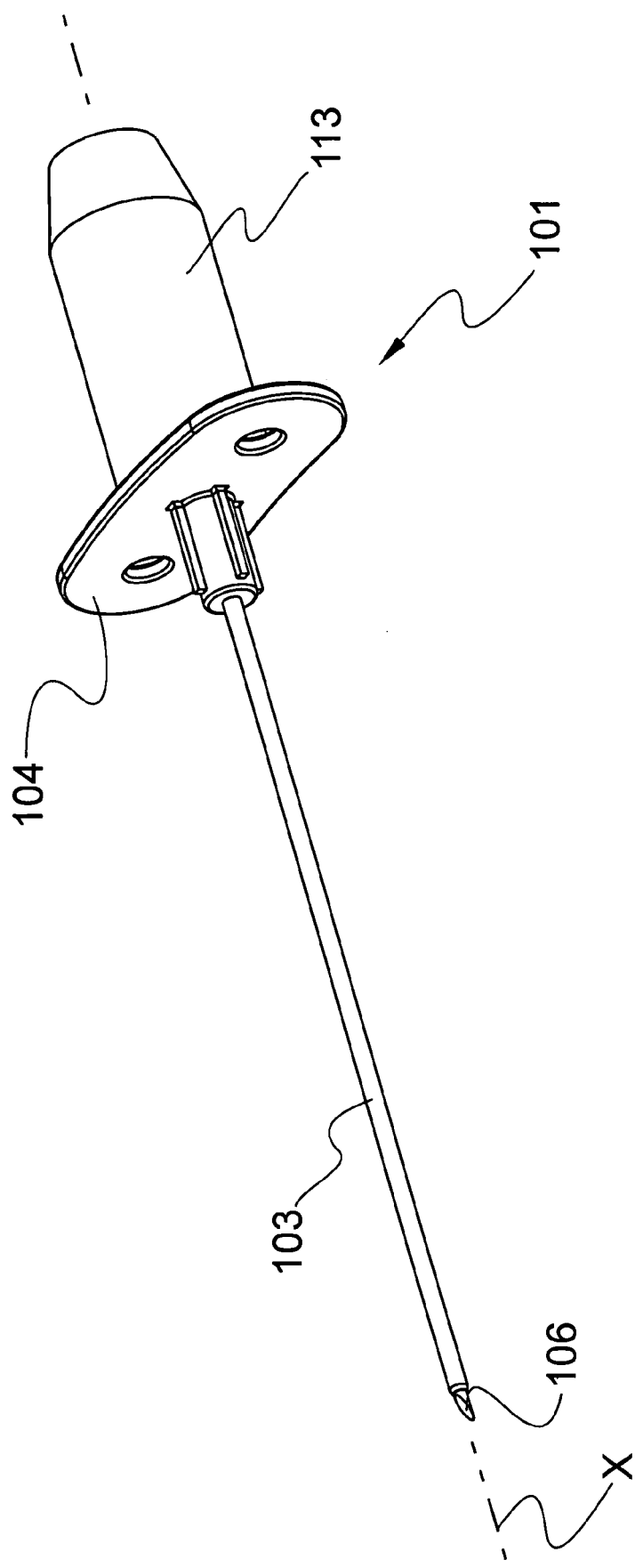
FIG. 1 is a perspective view of one particular embodiment of a medical needle shield apparatus in accordance with the principles of the present disclosure.

The exemplary embodiments of the medical needle shield apparatus and methods of operation disclosed are discussed in terms of medical needles for infusion of intravenous fluids, medication infusion or fluid collection, guiding of other needles, e.g., biopsy, and more particularly, in terms of needle shield apparatus employed with a needle cannula that prevent hazardous exposure to the needle tip, including, for example, inadvertent needle sticks. It is envisioned that the present disclosure, however, finds application to a wide variety of cannula needles and devices for the infusion of preventive medications, medicaments, therapeutics, etc. to a subject, such as, for example, epidural needles, spinal needles, biopsy needles, chiba needles, potts cournand needles, coaxial introducer needles, Y-sites, etc. It is also envisioned that the present disclosure may be employed for collection of body fluids and/or tissues, including those employed during procedures relating to soft tissue biopsy, bone biopsy, phlebotomy, digestive, intestinal, urinary, veterinary, etc. It is contemplated that the medical needle shield apparatus may be utilized with other medical needle applications including, but not limited to, fluid infusion, fluid collection, catheters, catheter introducers, guidewire introducers, biopsy needle introducers, spinal and epidural, biopsy, aphaeresis, dialysis, blood donor, Veress needles, Huber needles, etc.

In the discussion that follows, the term "proximal" refers to a portion of a structure that is closer to a clinician, and the term "distal" refers to a portion that is further from the clinician. As used herein, the term "subject" refers to a patient that receives infusions or has blood and/or fluid collected therefrom using the medical needle shield apparatus. According to the present disclosure, the term "clinician" refers to an individual administering an infusion, performing fluid or tissue collection, installing or removing a needle cannula from a medical needle shield apparatus and may include support personnel.

The following discussion includes a description of the medical needle shield apparatus, followed by a description of the method of operating the medical needle shield apparatus in accordance with the present disclosure. Reference will now be made in detail to the exemplary embodiments of the disclosure, which are illustrated in the accompanying figures.

Turning now to the figures, wherein like components are designated by like reference numerals throughout the several views. Referring initially to FIGS. 1–11, there is illustrated a medical needle shield apparatus, constructed in accordance with the principals of the present disclosure. The medical needle shield apparatus includes a shield 101 that is extensible from a retracted position (FIGS. 1, 3) to an extended position (FIGS. 2, 4) to enclose a distal end 115 of a needle such as, for example, stylet 106 of a needle assembly. The needle assembly includes a hollow outer needle 103. Stylet 106 is slideably and concentrically disposed with needle 103 for employment therewith during a medical needle application, as will be discussed. A stylet handle 113 is connected to stylet 106 to facilitate manipulation thereof. Other needle assemblies are also contemplated, including for example, needle cannulae, guide wire/introducers, etc.

A binding member 105 is disposed within shield 101 and defines binding surfaces 122. Binding surfaces 122 form an aperture configured for slidable receipt of stylet 106 between the retracted position and the extended position. Binding member 105 includes a drag inducing member, such as, for example, friction members 126 extending therefrom. Binding member 105 has a stylet communicating surface 123 that is engageable with stylet 106 to prevent rotation to the binding position of binding member 105.

Friction members 126 are configured for slidable engagement with stylet 106 between the retracted position and the extended position such that friction members 126 engage stylet 106 to create a drag force with stylet 106. It is envisioned that one or a plurality of friction members 126 may be employed.

Figure 4:
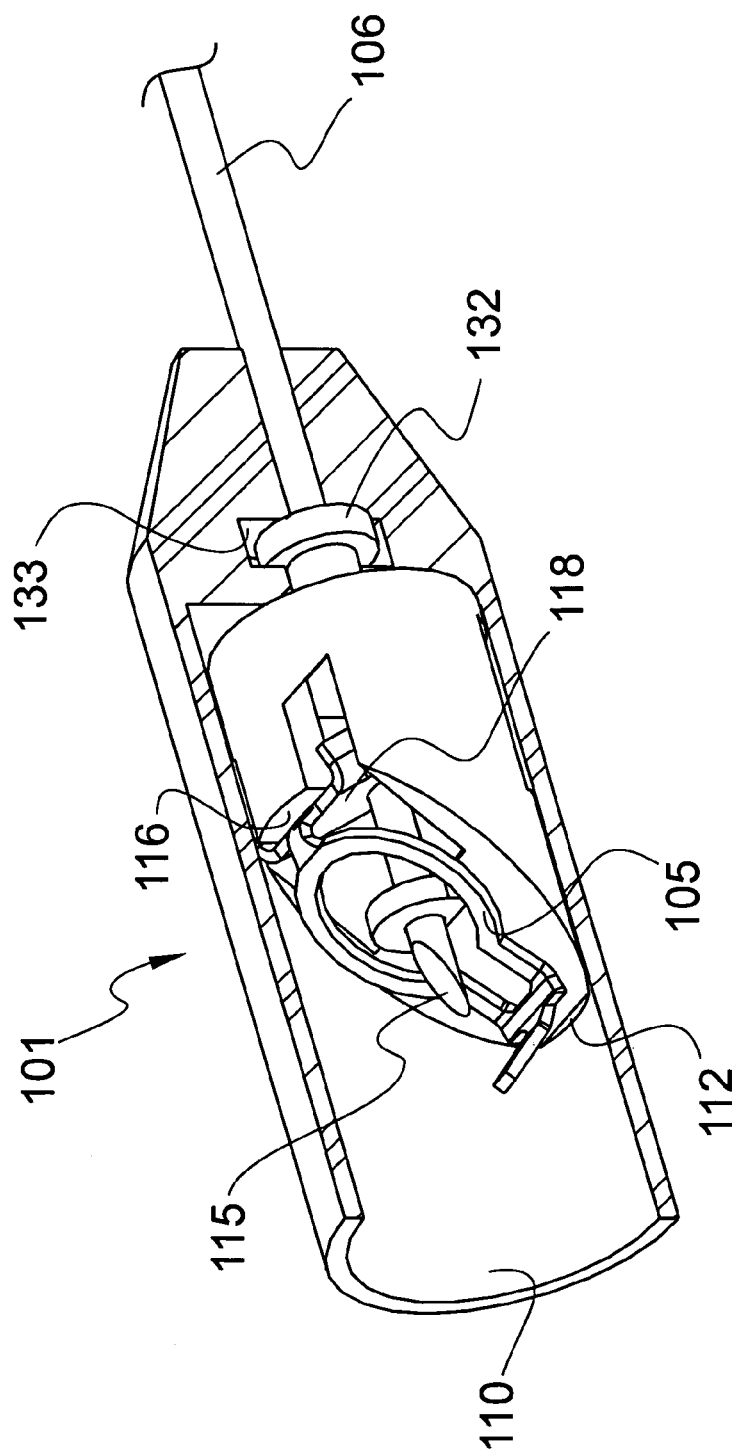
FIG. 4 illustrates the cutaway perspective view of the medical needle shield apparatus shown in FIG. 2 in a binding orientation.
Figure 5:
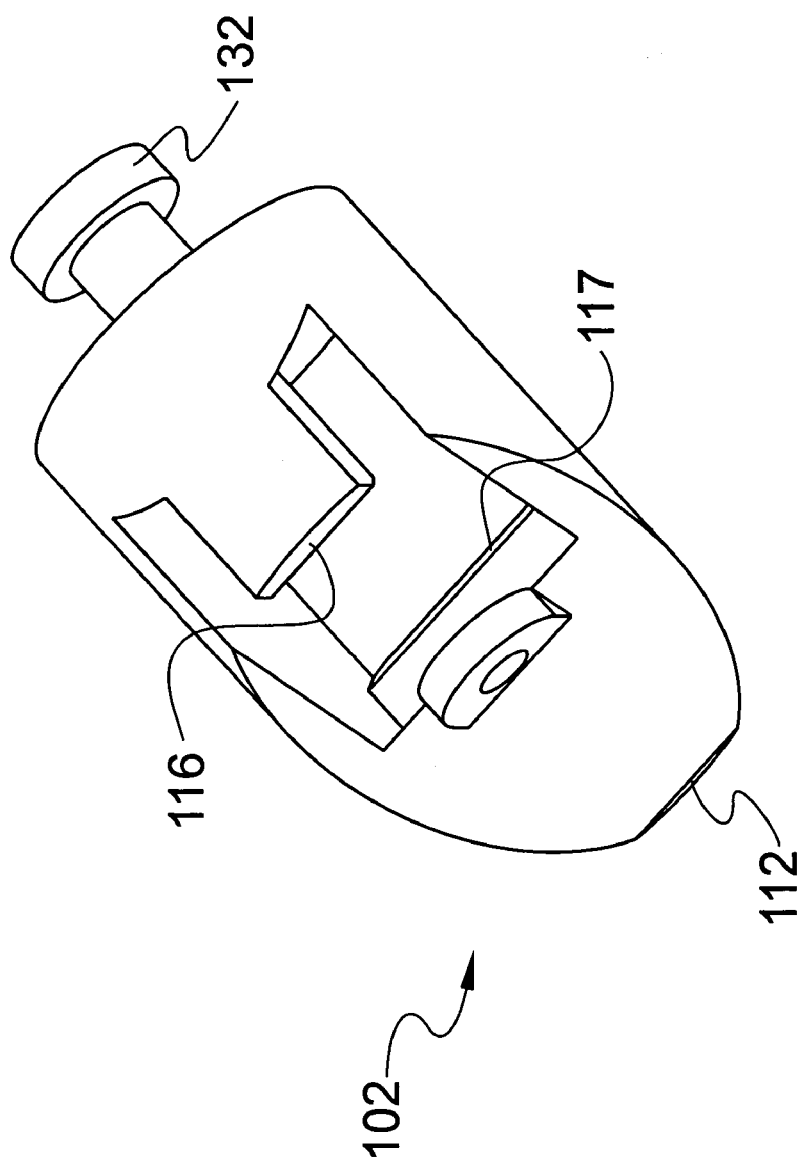
FIG. 5 is a perspective view of the housing of a needle safety apparatus as shown in FIG. 1.
Figure 6:
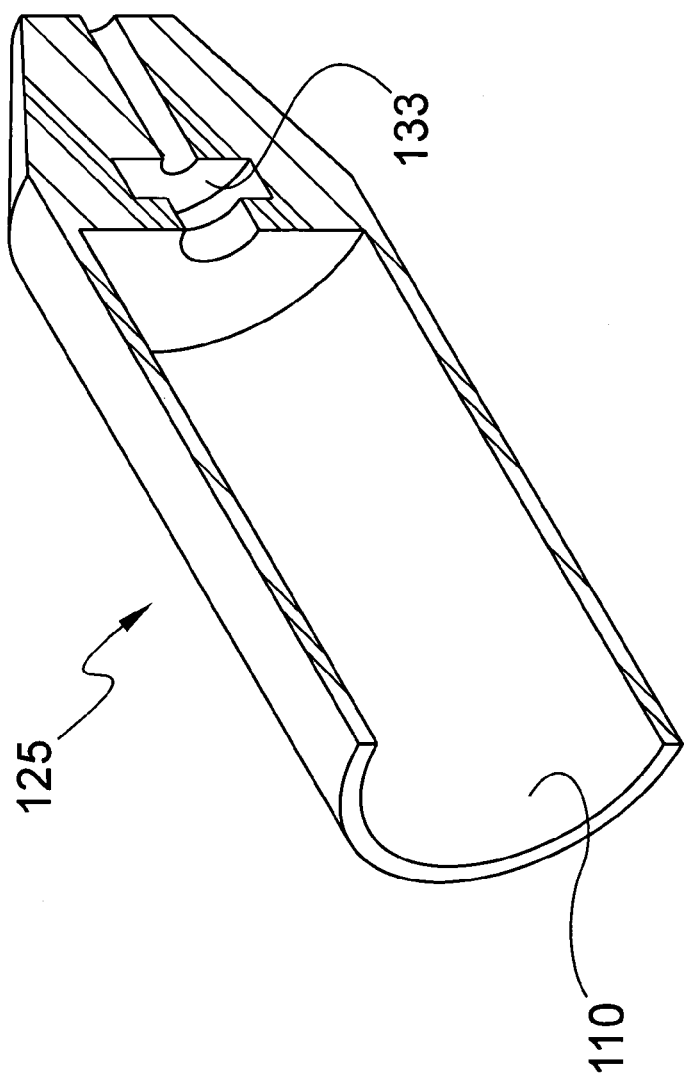
FIG. 6 is a cutaway perspective of the grip element of a needle safety apparatus as shown in FIG. 1.
Figure 7:
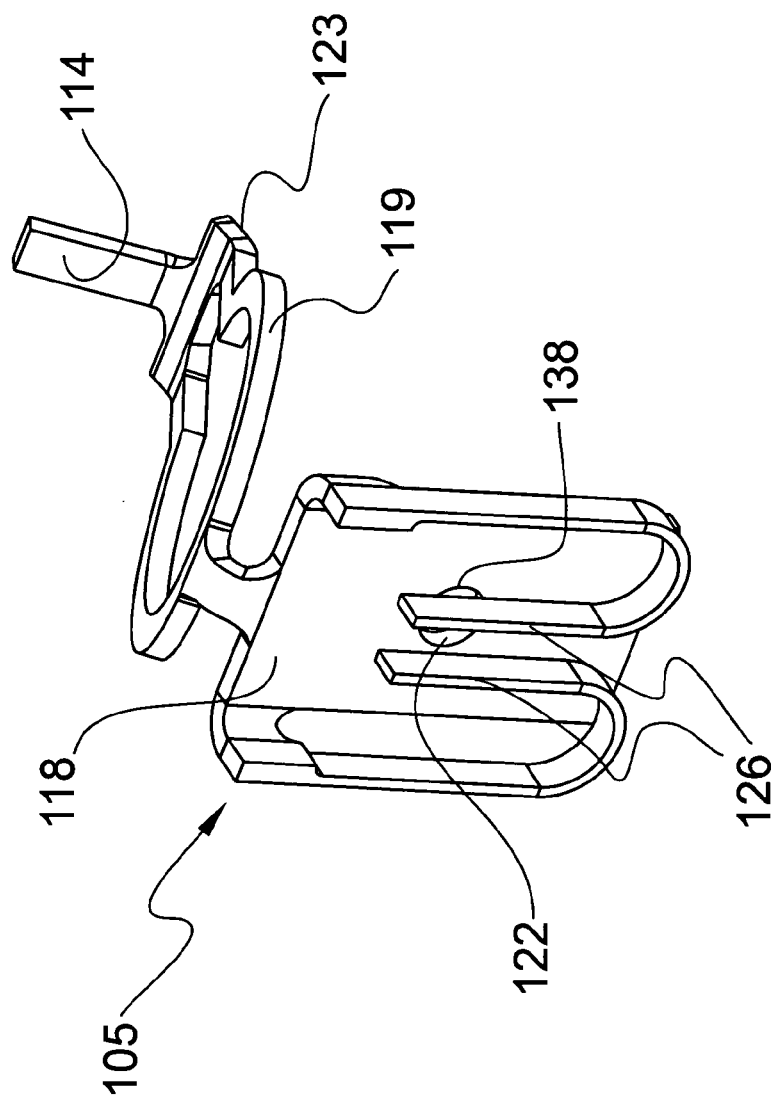
FIG. 7 is an enlarged perspective view of a binding member of the medical needle shield apparatus shown in FIG. 1.
Figure 8:
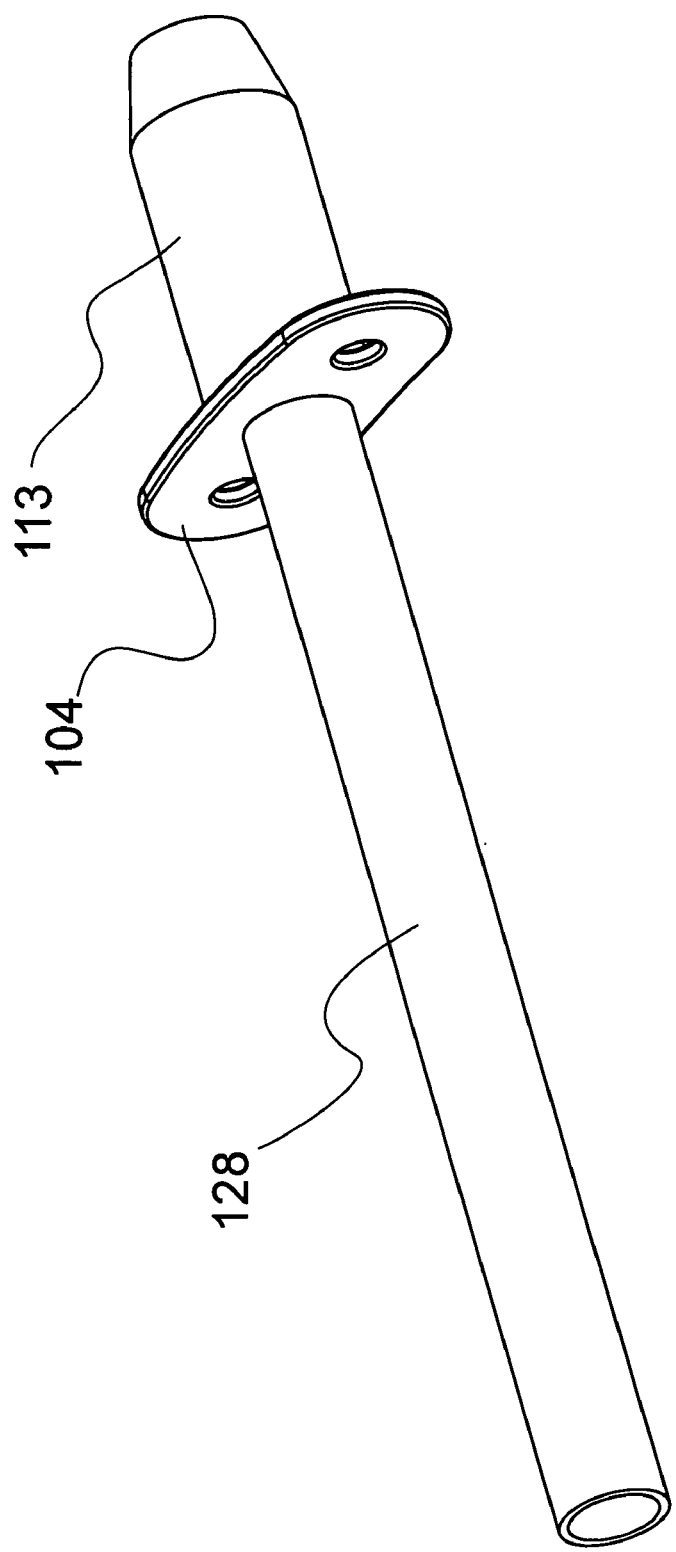
FIG. 8 is a perspective view of the needle shield apparatus as shown in FIG. 1 having a protective needle sheath installed thereon.
Figure 9:
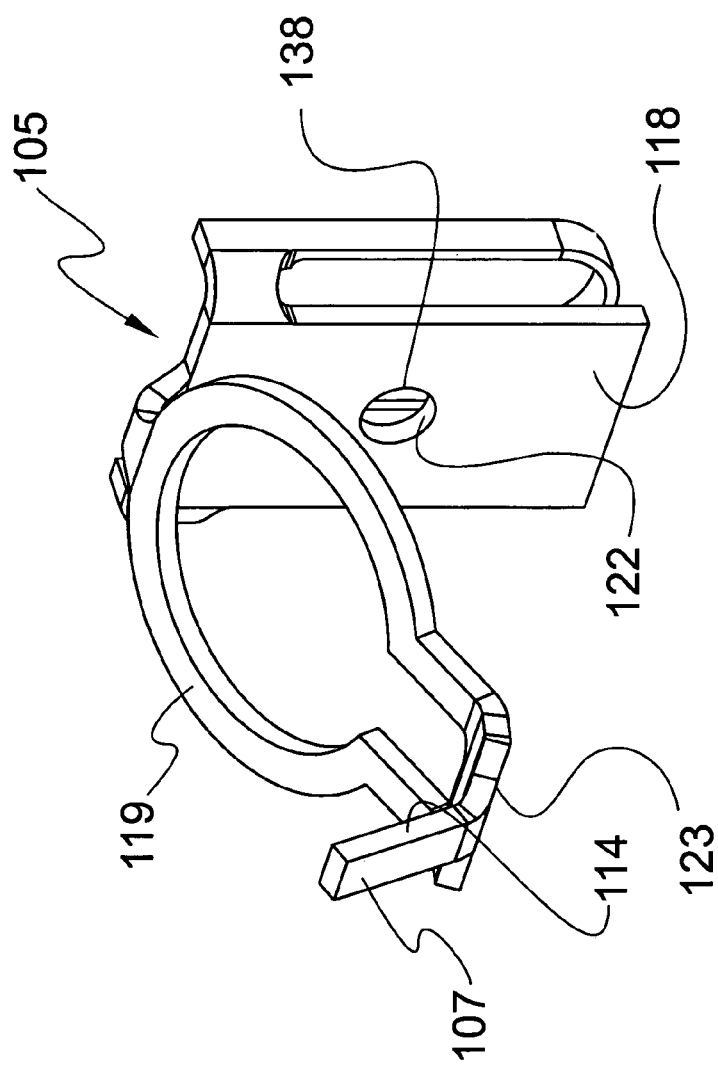
FIG. 9 is an alternate enlarged perspective view of the binding member shown in FIG. 7.
Figure 10:
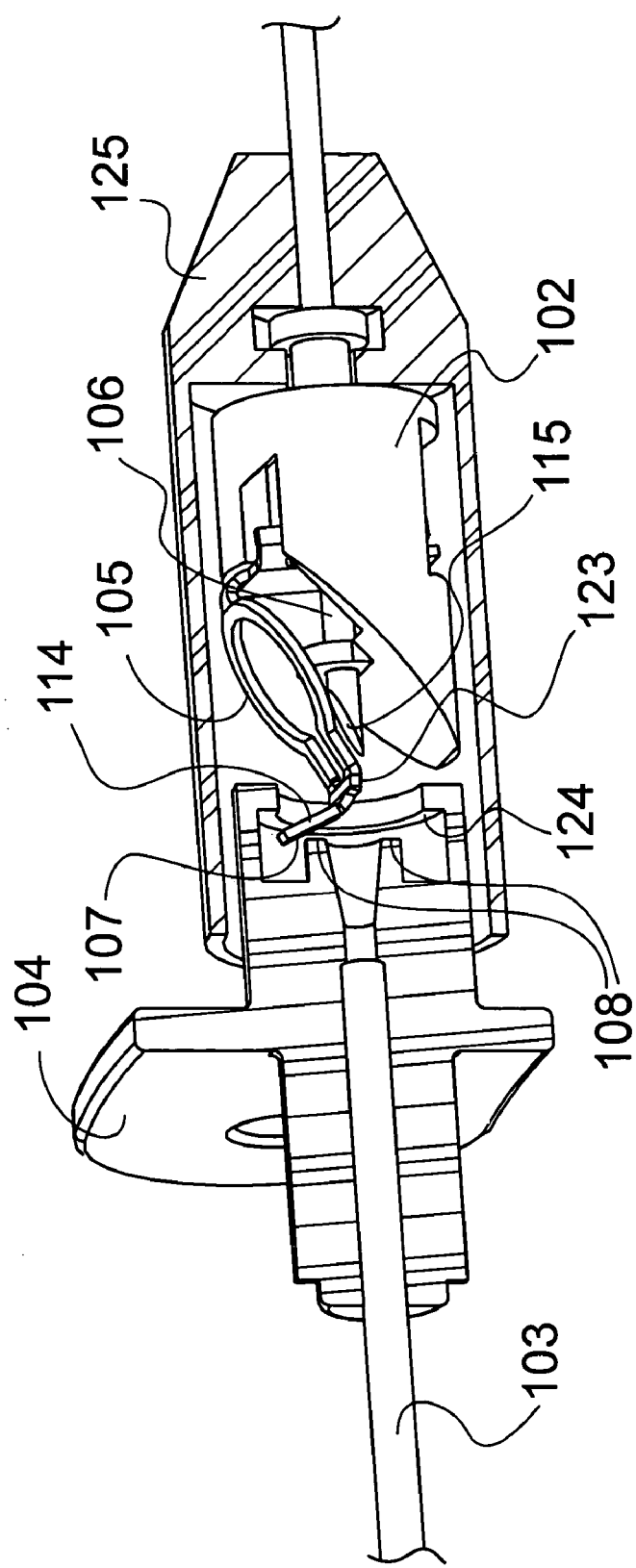
FIGS. 10–11 are cutaway perspective views of the medical needle safety apparatus showing engagement between hub reset surface and binding member reset surface according to the present disclosure.

The drag force in conjunction with one of blocking members 116 and/or 117, cause binding member 105 to move to a binding position (FIG. 4). The force created by blocking members 116 and/or 117 acts in a direction opposite to the drag force. This causes a force couple, which moves binding member 105 to the binding position.

As stylet 106 is released from engagement with a stylet communicating surface 123, binding member 105 and a retainer 114 move to the binding position. Rotation of binding member 105 is no longer opposed by engagement with stylet 106 at stylet communicating surface 123. Thus, binding member 105, with retainer 114, is subject to inclination into the binding position. Rotation of binding member 105 causes binding surfaces 122 to frictionally engage stylet 106 to prevent movement thereof.

Blocking members 116 and/or 117 cause binding member 105 to move to the binding position as forces imposed on shield 101 cause relative movement thereof in either direction along longitudinal axis x. This maintains stylet 106 within shield 101 to avoid hazardous exposure to distal end 115. It is envisioned that stylet communicating surface 123 may include ribs, projections, cavities, etc. for engagement with stylet 106 or that a portion of stylet communicating surface 123 engages stylet 106.

The components of the medical needle shield apparatus can be fabricated from a material suitable for medical applications, such as, for example, polymerics or metals, such as stainless steel, depending on the particular medical application and/or preference of a clinician. Semi-rigid and rigid polymerics are contemplated for fabrication, as well as resilient materials, such as molded medical grade polypropylene. However, one skilled in the art will realize that other materials and fabrication methods suitable for assembly and manufacture, in accordance with the present disclosure, also would be appropriate.

In an illustrative embodiment, shield 101 includes a bearing 102 that houses binding member 105. Bearing 102 may be monolithically formed or integrally assembled of multiple sections and may be substantially transparent, opaque, etc.

In the retracted position, shield 101 is disposed adjacent to a needle hub 104 of outer needle 103. It is contemplated that outer needle 103 may also be comprised of a flexible, polymeric material, and that the components of the medical needle apparatus may be employed with other needle applications, such as, for example, catheters, PICC introducers, etc.

Binding member 105 may be monolithically formed and includes an aperture plate 118, frictional members 126, end sensing member 119, stylet communicating surface 123, binding member reset surface 107 and retainer 114. It is contemplated that binding member 105 may include one or more frictional members 126, and that retainer 114 may extend from bearing 102. Aperture plate 118 may have a rectangular, generally planar configuration with sufficient stiffness to produce forces for binding stylet 106, as will be discussed. It is envisioned that aperture plate 118 may have an arcuate surface, undulating, etc. It is further envisioned that aperture plate 118 may have various degrees of stiffness according to the requirements of a particular application.

The embodiment of a resettable passive safety device disclosed in FIGS. 1–11 show a hollow needle 103 solid stylet 106, rotational housing with a stylet shield 125 and thrust bore 133, a bearing 102 with thrust collar 132, and a binding member 105. The thrust bore 133 and thrust collar 132 are configured to allow rotation of stylet shield 125 relative to bearing 102.

The resettable feature of this device is employed after the passive safety device has been activated. Initially, the safety shield 101 and needle 103 are positioned over the stylet 106 (FIG. 1). During the medical procedure, the stylet 106 is automatically protected by the safety shield 101 as the stylet 106 is withdrawn from the needle (FIG. 2).

Figure 3:
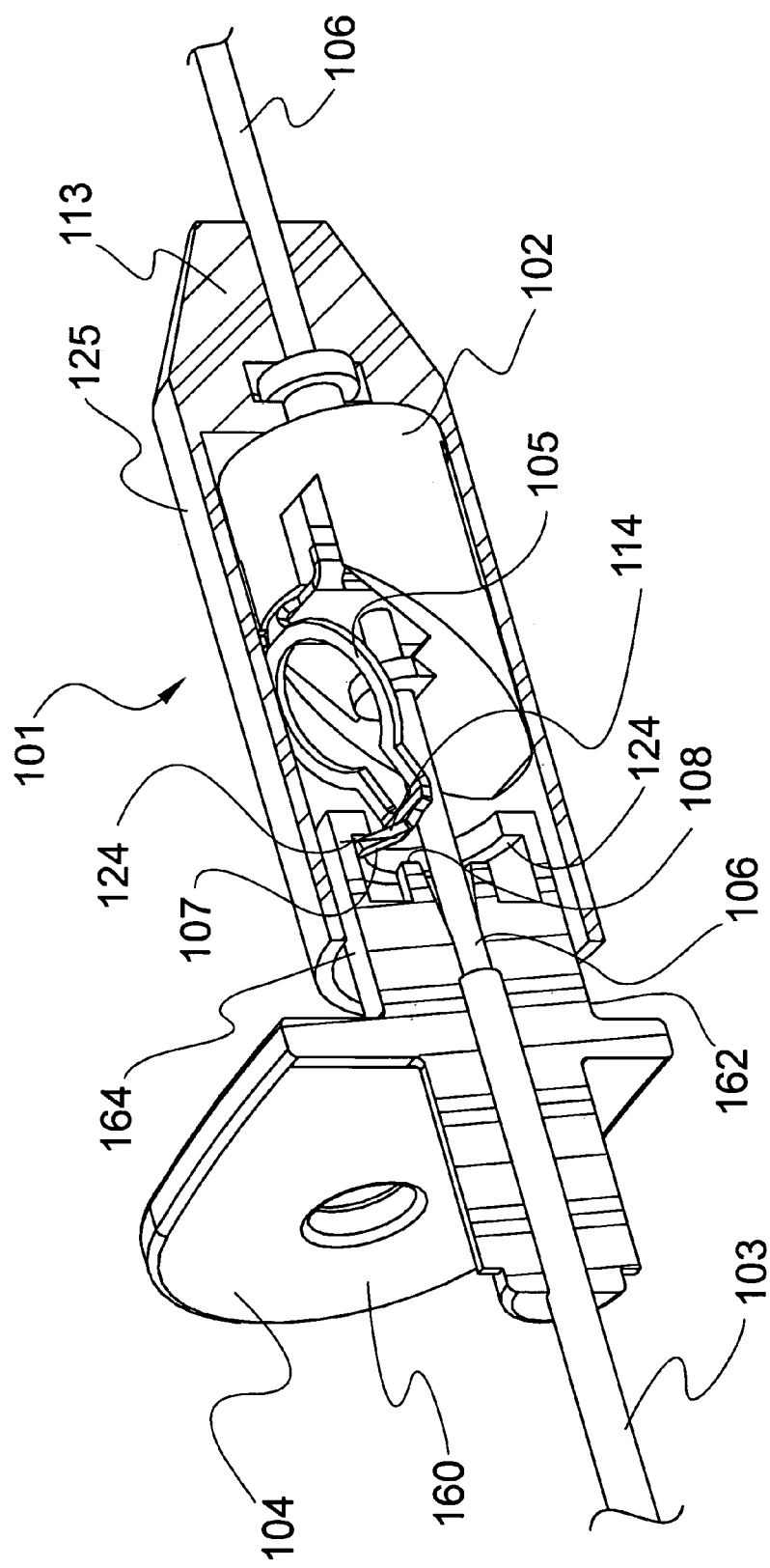
FIG. 3 is a cutaway perspective view of a shield of the medical needle shield apparatus shown in FIG. 1 in a non-binding orientation.

The safety shield 101 is advanced to near the distal end of the stylet 115 in a position prior to activation of the binding member 105 (FIG. 3). In this position, the hub retainer 114 retains the proximity of the needle hub 104 to the safety shield 101 by interacting with hub slot 124 and the binding member 105 is in the sliding orientation. It is envisioned that hub slot 124 may be in the form of other shapes for providing a cavity.

In FIG. 4, the safety shield 101 is positioned further toward the distal end of the stylet 115 to the point where the safety shield 101 is activated. The binding member 105 has moved to the binding orientation and the hub retainer 114 of the binding member 105 has released the needle hub 104.

Figure 2:
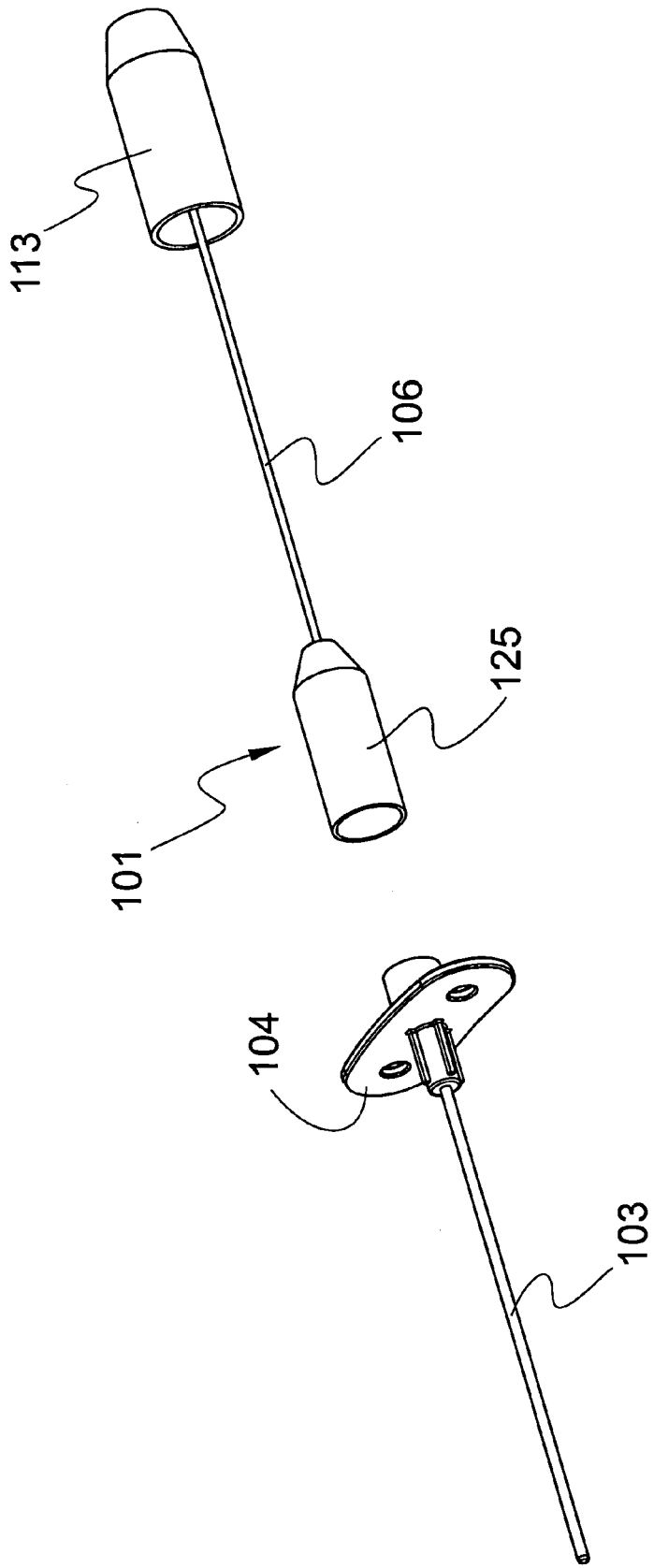
FIG. 2 is a perspective view of the embodiment shown in FIG. 1 in a shielded configuration.

In FIG. 2, the activated and locked safety shield 101 is illustrated. In this configuration, the needle 103 has been removed, the stylet distal end 115 is inside the housing at a distance which prevents human contact, and the binding member 105 is in the binding orientation.

Frictional members 126 may be monolithically formed with binding member 105 and extend from aperture plate 118 in association therewith for alignment with aperture 138 and engagement with stylet 106. Such engagement creates a frictional drag force with stylet 106. This frictional drag force in conjunction with one of the blocking members 116 and/or 117 causes binding member 105 to move with stylet 106, which generates a canting force and inclination of aperture plate 118. The canting force and inclination urge rotation of binding member 105. It is contemplated that a single friction member may be employed. It is further contemplated that frictional members 126 may have flexible portions, which may be of varying flexibility according to the particular requirements of a needle application.

As facilitated by movement of stylet 106, the canting force causes a lever or moment of end sensing member 119, which is opposed to prevent rotation of binding member 105. The canting force is opposed by engagement of stylet communicating surface 123 with stylet 106 in a non-binding or sliding orientation (FIG. 3) of binding member 105.

End sensing member 119 extends distally from aperture plate 118. End sensing member 119 may be perpendicularly oriented relative to a plane defined by aperture plate 118. This perpendicular orientation facilitates inclination of aperture plate 118 for disposal in a binding or non-binding orientation of binding member 105. It is envisioned that end sensing member 119 may be variously oriented with aperture plate 118 and may flexibly extend therefrom.

Stylet communicating surface 123 opposes the canting force of end sensing member 119 directed to stylet 106. The canting force is generated by friction members 126 in conjunction with one of blocking members 116 and/or 117 and facilitates inclination of aperture plate 118. Inclination, however, is prevented in the non-binding or sliding orientation because of the engagement of stylet communicating surface 123 with stylet 106. As stylet 106 is retracted proximally and shield 101 is extended distally, stylet 106 continues to slideably engage stylet communicating surface 123.

As stylet 106 is released from engagement with stylet communicating surface 123, as shown in FIG. 4, a drag force is created between friction members 126 and stylet 106. The drag force in conjunction with blocking member 116, cause aperture plate 118 to move to the binding position, as discussed.

Rotation of aperture plate 118 causes binding surfaces 122 to frictionally engage stylet 106 to prevent movement thereof. Blocking members 116, 117 cause aperture plate 118 to move to the binding position as forces are imposed on shield 101 in either direction along longitudinal axis x. This maintains stylet 106 within shield 101 to avoid hazardous exposure to distal end 115.

Aperture 138 is formed within aperture plate 118 for slidable engagement with stylet 106 during movement between the retracted position and the extended position of shield 101. Aperture 138 includes binding surfaces 122 formed on opposing sides of aperture 138 that engage stylet 106 to prevent movement thereof in the extended position of shield 101. It is contemplated that engagement to prevent movement of stylet 106 may include penetrating, frictional, interference, etc. It is envisioned that aperture 138 may have various geometric configurations, such as radial, polygonal, etc. It is further envisioned that aperture 138 may define an open cavity within aperture plate 118, such as, for example, "U" shaped and open to one or a plurality of edges of aperture plate 118.

The inclination of aperture plate 118 relative to longitudinal axis x facilitates sliding and binding, via binding surfaces 122, of stylet 106 within shield 101 to prevent hazardous exposure to distal end 115. For example, as shown in FIG. 3, aperture plate 118 is oriented at an angle of approximately 90° relative to longitudinal axis x such that aperture plate 118 is disposed substantially perpendicular to stylet 106. In this non-binding or sliding orientation, stylet 106 is free to slide within aperture 138. As stylet 106 is retracted and shield 101 is extended, stylet 106 continues to engage stylet communicating surface 123 and aperture plate 118 maintains its perpendicular orientation relative to longitudinal axis x.

Referring to FIG. 4, shield 101 is manipulated such that friction members 126 in conjunction with blocking member 116 cause binding member 105 to rotate relative to longitudinal axis x. Aperture plate 118 rotates out of perpendicular alignment with stylet 106 such that aperture plate 118 is oriented at an angle less than 90° with respect to longitudinal axis x.

As aperture plate 118 rotates, the binding member 105 approaches a binding orientation. The binding orientation includes engagement of binding surfaces 122 with stylet 106 due to the binding orientation of aperture plate 118. This engagement creates binding frictional forces on stylet 106, in conjunction with frictional members 126 and blocking members 116, 117 to prevent movement of stylet 106 relative to shield 101 in both distal and proximal directions, and to maintain distal end 115 within shield 101 to prevent hazardous exposure thereto.

Blocking members 116, 117 are disposed not to interfere with stylet 106. Blocking members 116, 117 define surfaces that facilitate disposal of aperture plate 118 in a binding orientation.

For example, as shown in FIG. 3, shield 101 is in a retracted position and stylet 106 is fully extended. Binding member 105 and aperture plate 118 are in a non-binding or sliding orientation such that aperture plate 118 is substantially perpendicular to longitudinal axis x. Blocking members 116, 117 may engage aperture plate 118 to maintain aperture plate 118 in the perpendicular orientation. Blocking members 116, 117 may also maintain such orientation during extension of stylet 106 or may not engage stylet 106.

As stylet 106 is retracted and shield 101 is extended, as shown in FIG. 4, friction members 126 create a drag force via engagement with stylet 106 on binding member 105 and in conjunction with blocking member 116 cause aperture plate 118 to rotate in a counter-clockwise direction to the binding position. Blocking members 116, 117 engage aperture plate 118 to facilitate rotation thereof from the perpendicular position into the binding position such that binding surfaces 122 engage stylet 106, as discussed. This configuration prevents movement of stylet 106.

Binding of binding member 105 to stylet 106 is facilitated by the friction force generated between binding surfaces 122 and stylet 106. This frictional engagement prevents axial movement of stylet 106 relative to bearing 102 when shield 101 is in the extended position. This configuration advantageously prevents hazardous exposure to stylet 106. It is contemplated that binding surfaces 122 may include sharp edges to increase frictional engagement. It is further contemplated that the binding friction force may be created and varied by one or more altering factors, such as, for example, aperture 138 configuration and dimension, stylet 106 configuration and dimension, aperture plate 118 thickness, the dimension from blocking members 116, 117 contact point to the centerline of stylet 106 and the coefficient of friction between aperture 138 and stylet 106 depending on the particular requirements of a needle application. It is envisioned that friction members 126 may be configured so as to vary the drag force with variation of the inclination of the aperture plate 118, this variation in drag force may be accomplished by geometric changes in the shape of the friction members 126, such as wedge shapes or the inclusion of notches to engage stylet 106, this variation in drag force may also be accomplished through the selective application of friction modifying materials or coatings such as oils, jells, greases, or coatings which change the friction.

It is envisioned that the aperture in aperture plate 118 may create a drag force via engagement with sylet 106 to cause rotation of binding member 105, similar to that described. It is further envisioned that materials such as, for example, jells, greases, etc. may be employed to create a frictional drag force with stylet 106 to cause rotation of binding member 105.

Needle hub 104 is mounted with needle 103 and is releasably mounted with shield 101 via releasable engagement with retainer 114. Needle hub 104 is employed with the medical needle shield apparatus of the present disclosure for various utility according to the requirements of a particular medical needle application. Shield 101 and needle hub 104 slidably support needle 103 and stylet 106 for use thereof. Handle 113 facilitates manipulation thereof.

Needle hub 104 has a hub slot 124 for receipt and engagement with binding member 105. Needle hub 104 has a finger tab 160 for urging needle hub 104 in a direction, along longitudinal axis x, away from shield 101. This configuration facilitates removal and use of needle hub 104 and needle 103 from shield 101 during a medical needle application. It is contemplated that finger tab 160 may be alternatively configured and dimensioned according to the needle application.

A flange 162 of needle hub 104 is concentrically supported by a control surface 110 disposed about an inner surface of bearing 102. Control surface 110 engages an outer surface 164 of flange 162 for releasable support thereof. Outer surface 164 may engage control surface 110 in a frictional, interference, etc. fit to maintain releasable positioning with bearing 102. It is contemplated that control surface 110 may engage other portions of needle hub 104.

Bearing 102 includes hub stop surfaces 112 that facilitate positioning of needle hub 104 with bearing 102. Hub stop surfaces 112 prevent proximal movement of needle hub 104 during mounting with and relative to bearing 102. Hub stop surfaces 112 advantageously facilitate control of the degree of insertion with bearing 102 according to the requirements of a particular medical needle application. One or a plurality of hub stop surfaces 112 may be employed. It is contemplated that hub stop surfaces 112 may include springs, clips, etc. to facilitate attachment with needle hub 104.

Retainer 114 may extend transversely from a distal end of stylet communicating surface 123. Hub retainer 114 extends a sufficient length for corresponding receipt within hub slot 124 of needle hub 104. In association with a non-binding or sliding orientation of binding member 105, retainer 114 engages needle hub 104, in hub slot 124, for releasably mounting with bearing 102 of shield 101.

As stylet 106 is retracted in a proximal direction and shield 101 is extended in a distal direction, retainer 114 rotates in a counter clockwise direction (FIG. 4) relative to longitudinal axis x due to the canting forces generated by friction members 126. Retainer 114 disengages from hub slot 124 to release needle hub 104 from bearing 102. A clinician may manipulate finger tab 160 to manipulate needle hub 104 distally and apart from shield 101. It is contemplated that retainer 114 may be variously oriented from binding member 105 or stylet communicating surface 123. It is further contemplated that hub slot 124 may be variously dimensioned to extend about the circumference of needle hub 104. Hub slot 124 may include tabs, etc. for retention with retainer 114.

To re-access the stylet distal end 115 using the resettable passive safety device, the stylet shield 125 is brought to mate concentrically with the proximal end of the needle hub 104, in a similar fashion to the pre-activated state of the device. As this occurs, the binding member reset surface 107 comes into contact with the hub reset surface 108. This action is depicted in the embodiment shown in FIG. 10.

As the stylet 106 is advanced from a proximal-to-distal direction, the hub reset surface 108 deflects the binding member reset surface 107, along with the end sensing member 119, to a position above the stylet 106 surface and urges the binding member 105 from the binding orientation to the sliding orientation. With the binding member 105 in the sliding orientation, the stylet 106 becomes free to advance into the needle 103.

Figure 11:
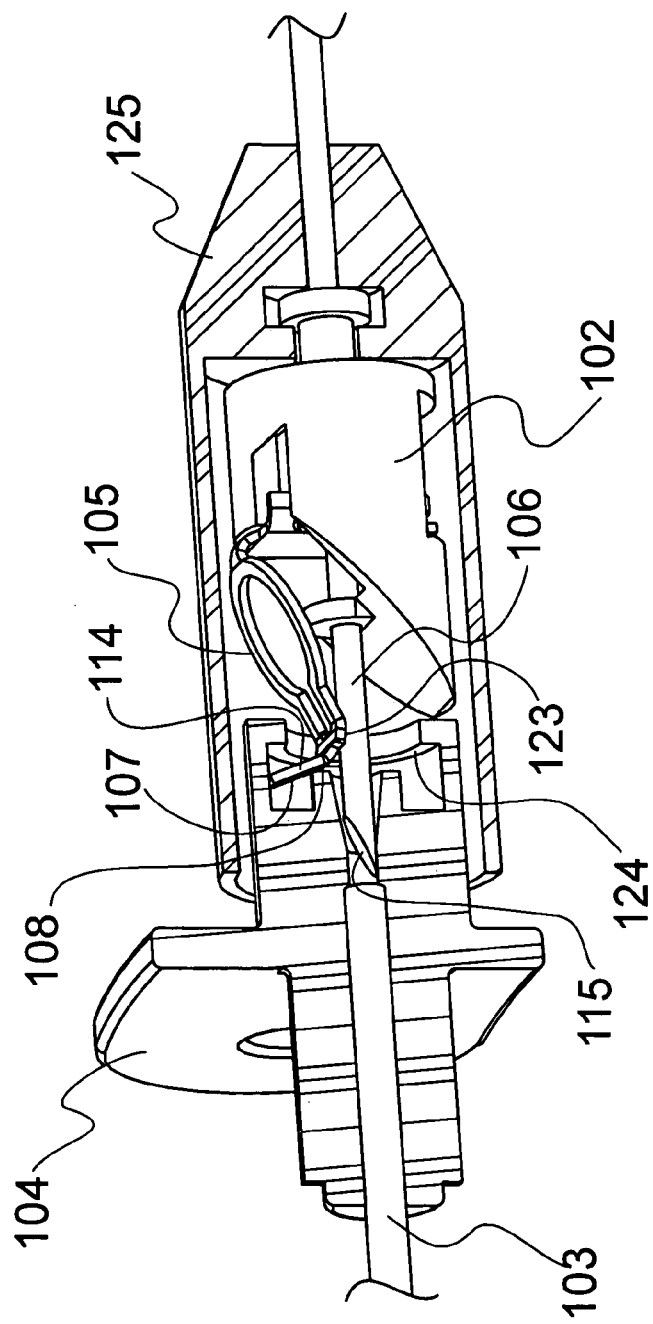
Figure 12:
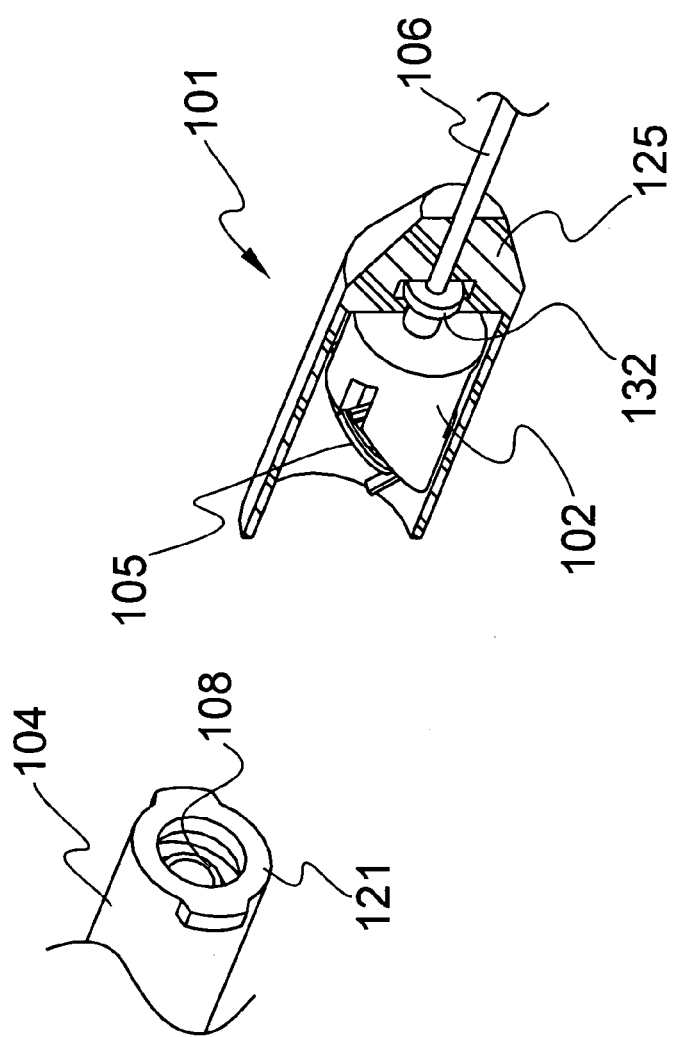
FIG. 12 is a cutaway perspective view of an embodiment of the medical needle safety apparatus according to the present disclosure adapted for use with a luer lock needle hub.
Figure 13:
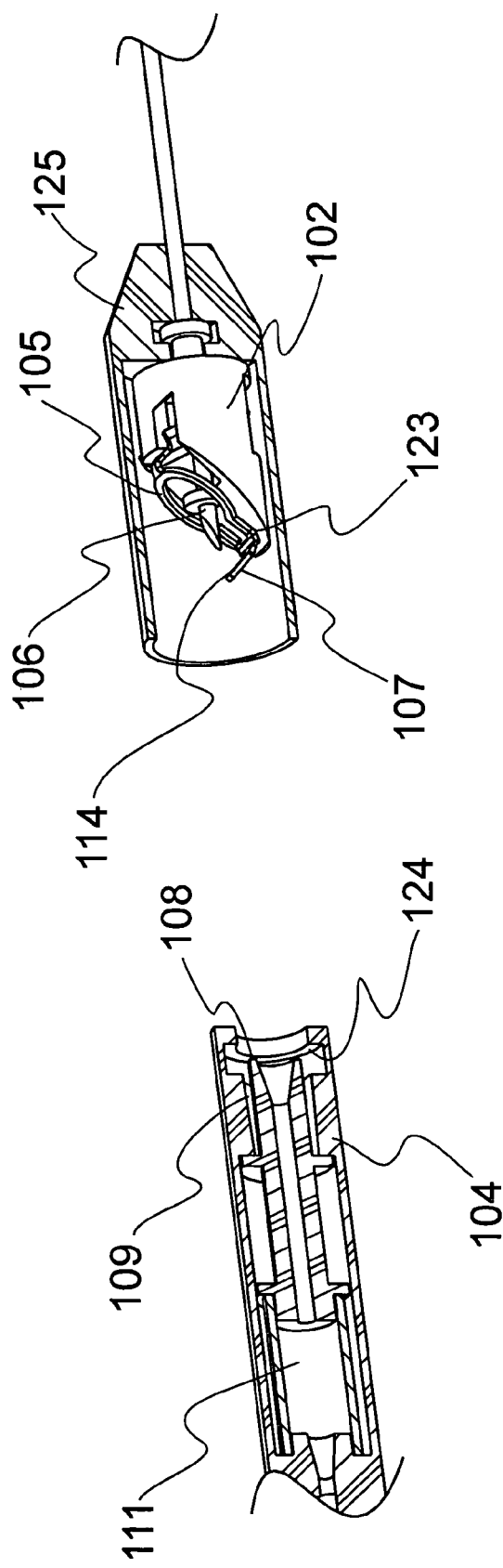
FIG. 13 is a cutaway perspective view the medical needle safety apparatus as shown in FIG. 12 in a shielded configuration.
Figure 14:
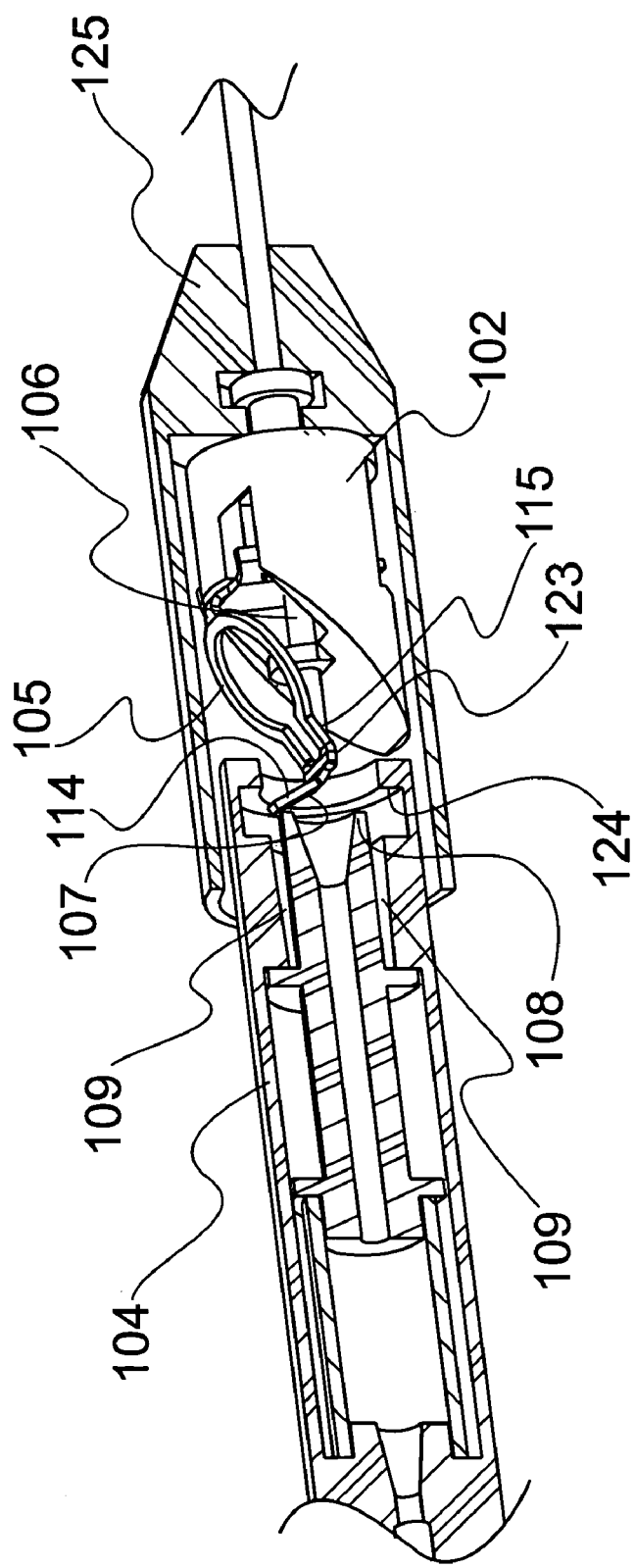
FIG. 14 is an enlarged perspective view of the medical needle safety apparatus as shown in FIG. 12 showing engagement between hub reset surface and binding member reset surface according to the present disclosure.

Concurrently, due to the contact between the hub reset surface 108 and the binding member reset surface 107, the hub retainer 114 is urged into the hub slot 124. This causes the hub retainer 114 of the binding member 105 to again retain the needle hub 104 to the safety shield 101 through the interaction with the hub slot 124 (FIG. 11).

Upon being reset, the safety shield 101 and needle 103 are positioned over the stylet 106, as seen in FIG. 1. During the medical procedure, the stylet 106 will be automatically protected by the safety shield 101 as the stylet 106 is again withdrawn from the needle.

FIGS. 12–15 illustrate the resettable safety shield according to the present disclosure as applied to a needle with a luer fitting 121 and a luer taper 109. In this embodiment, the hub reset surface 108 is provided on a portion separate from the needle hub 104. A hub reset surface spring 111 exerts a force to bias the hub reset surface 108 in the proximal direction. The hub reset surface spring 111 can be made from any number of suitable resilient materials commonly known, including metal, plastic, elastomeric materials, and the like.

Figure 23A:
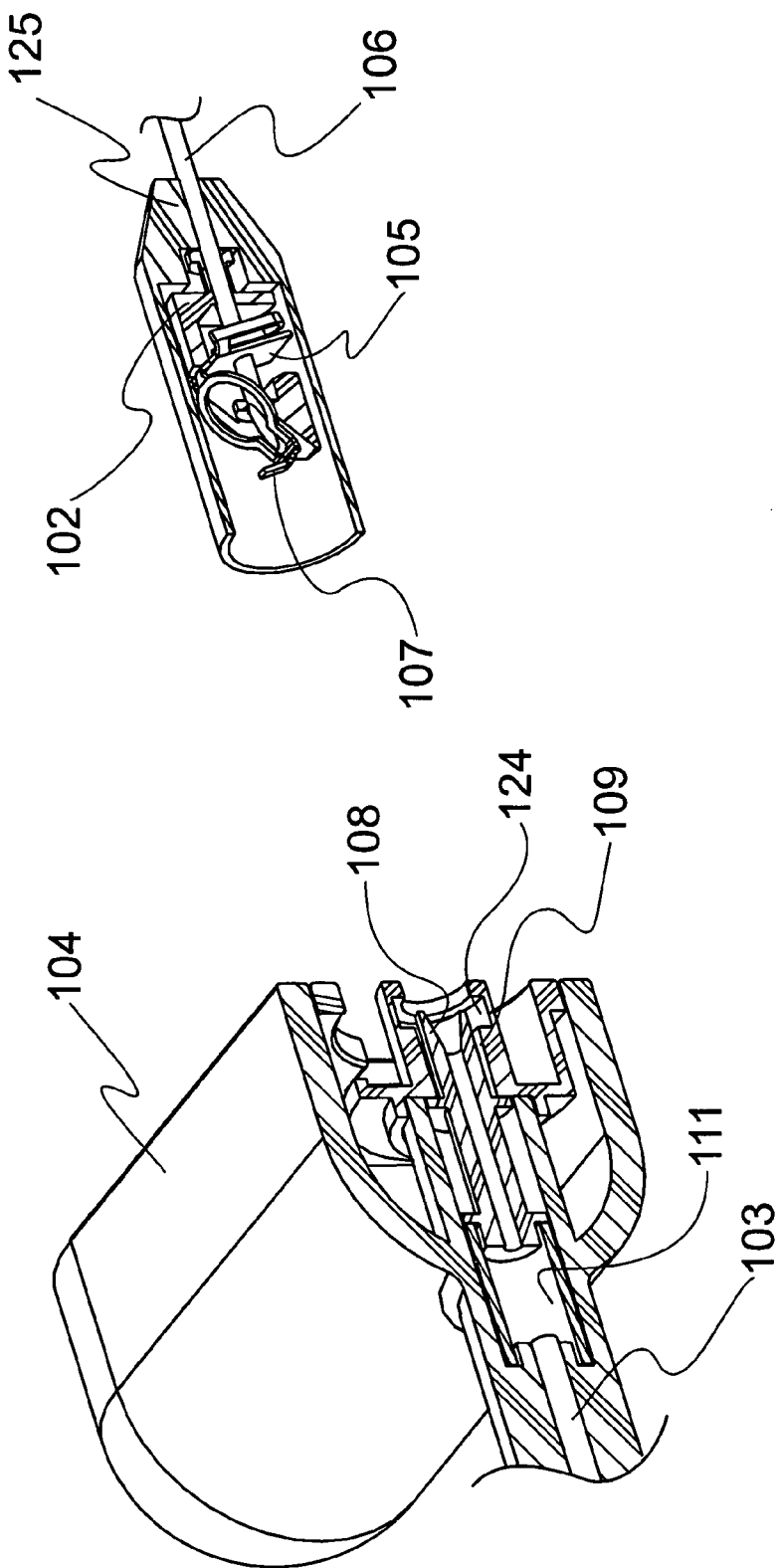
FIG. 23A is an enlarged cross-sectional view of the medical needle shield apparatus as shown in FIG. 22.
Figure 23B:
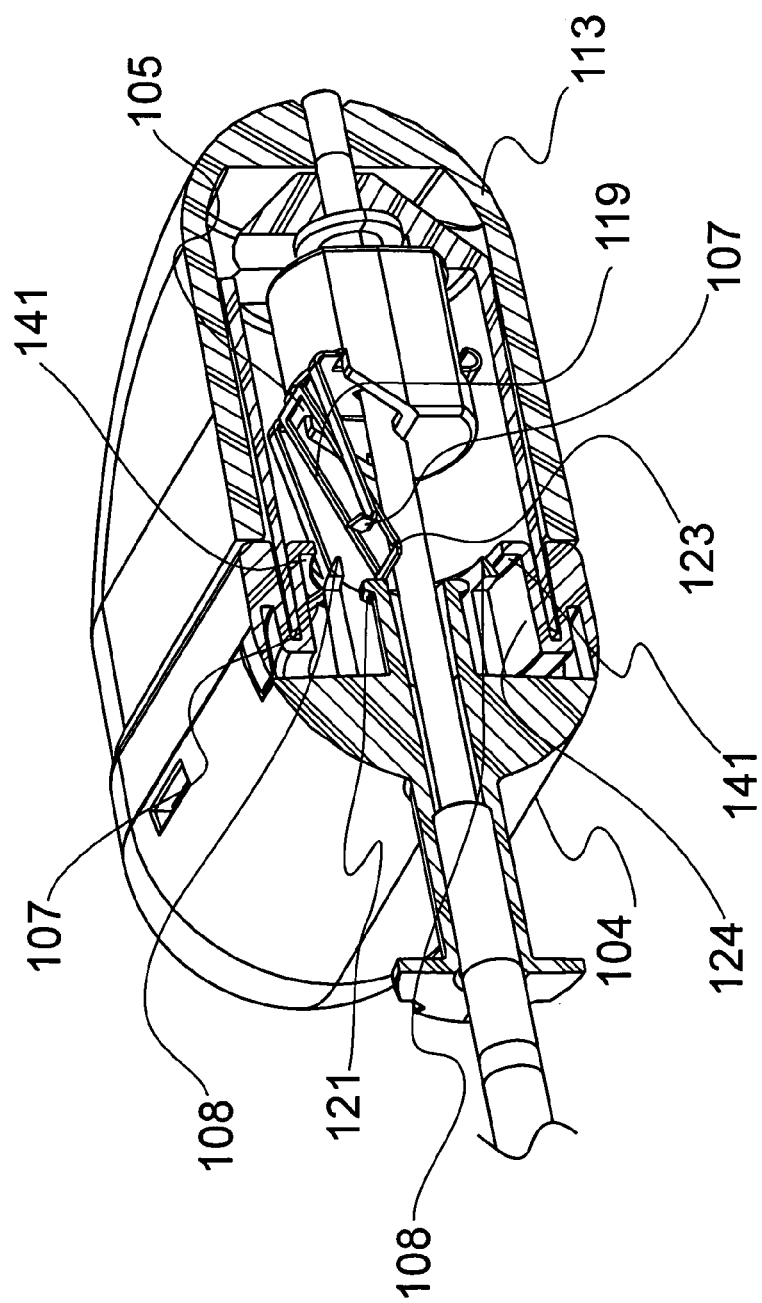
FIG. 23B is an enlarged cross-sectional view of an alternate embodiment of the medical needle shield apparatus shown in FIG. 22.

In the embodiment wherein the hub reset surface 108 is within the luer fitting 121, the hub reset surface spring 111 assures that the hub reset surface 108 is in the correct location in the needle hub to provide alignment and engagement between the hub reset surface 108 and binding member reset surface 107. When a luer male taper, such as for example, a luer lock or luer slip is inserted into needle hub 104, the hub reset surface spring 111 is compressed and the hub reset surface 108 is displaced to allow the luer male taper to mate with the entire length of luer taper 109. It is envisioned that the hub reset surface 108 may also be disposed around the luer fitting 121, as shown in FIG. 23B. The embodiment shown in FIG. 23B also shows an alternate embodiment of the reset surfaces 107 extending from the binding member 105 and engaging retaining surface 141.

To re-access the stylet distal end 115 using the resettable passive safety device, the stylet shield 125 is brought to mate concentrically with the proximal end of the needle hub 104, in a similar fashion to the pre-activated state of the device. As this occurs, the binding member reset surface 107 comes into contact with the hub reset surface 108. This action is depicted in the embodiment shown in FIG. 14.

As the stylet 106 is advanced from a proximal-to-distal direction, the hub reset surface 108 deflects the binding member reset surface 107, along with the end sensing member 119, to a position above the stylet 106 surface and urges the binding member 105 from the binding orientation to the sliding orientation. With the binding member 105 in the sliding orientation, the stylet 106 becomes free to advance into the needle 103.

Figure 15:
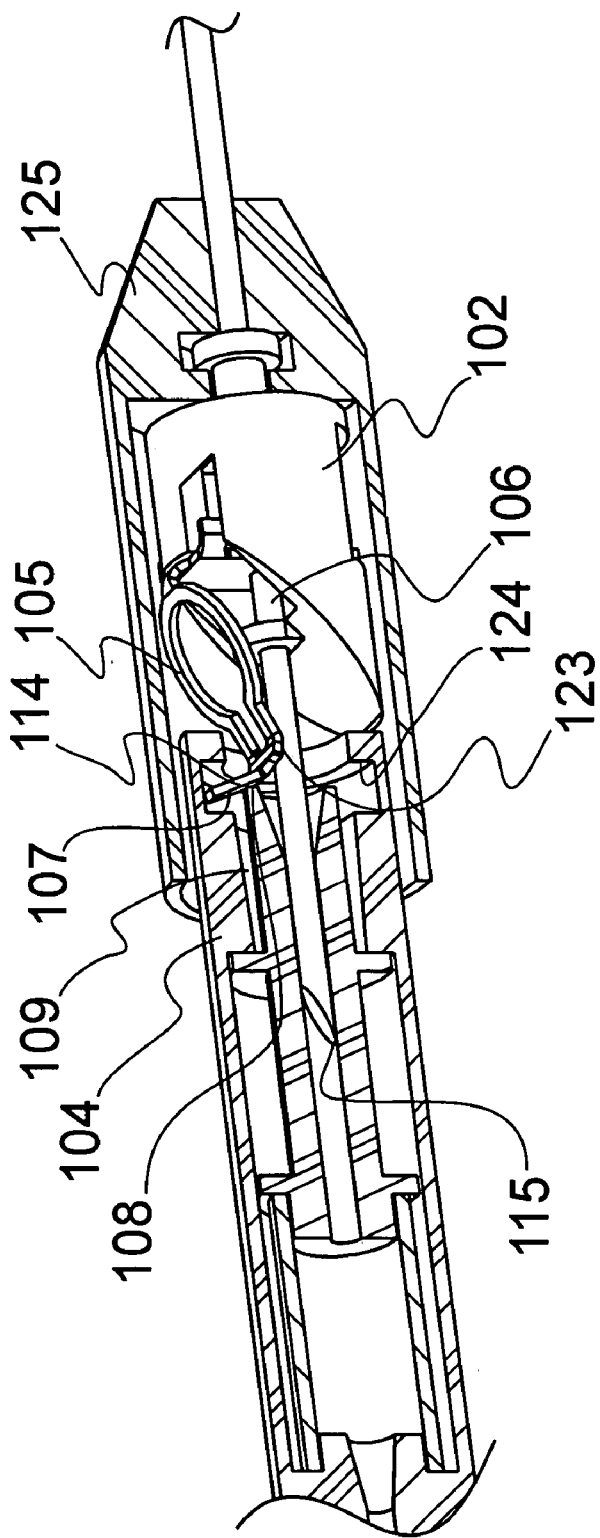
FIG. 15 is an enlarged perspective view of the medical needle safety apparatus as shown in FIG. 12 in a reset configuration.

Concurrently, due to the contact between the hub reset surface 108 and the binding member reset surface 107, the hub retainer 114 is urged into the hub slot 124. This causes the hub retainer 114 of the binding member 105 to again retain the needle hub 104 to the safety shield 101 through the interaction with the hub slot 124 (FIG. 15).

Upon being reset, the safety shield 101 and needle 103 are positioned over the stylet 106. During the medical procedure, the style 106 will be automatically protected by the safety shield 101 as the stylet 106 is again withdrawn from the needle.

FIGS. 16–27 illustrate the resettable safety shield according to the present disclosure as applied to a bone biopsy needle 101. In this embodiment, the luer taper 109 is used in the manner described hereinbefore with respect to FIGS. 12–15. The bone biopsy needle 101 may also include an adjustable depth stop assembly 140 for setting the desired needle 103 insertion depth. A lock nut 142 locks the depth stop assembly 140 in the desired position. Tabs 144 engage corresponding slots 156 (shown in FIG. 25) to fix depth stop assembly 140 while the lock nut 142 is engaged.

Figure 17:
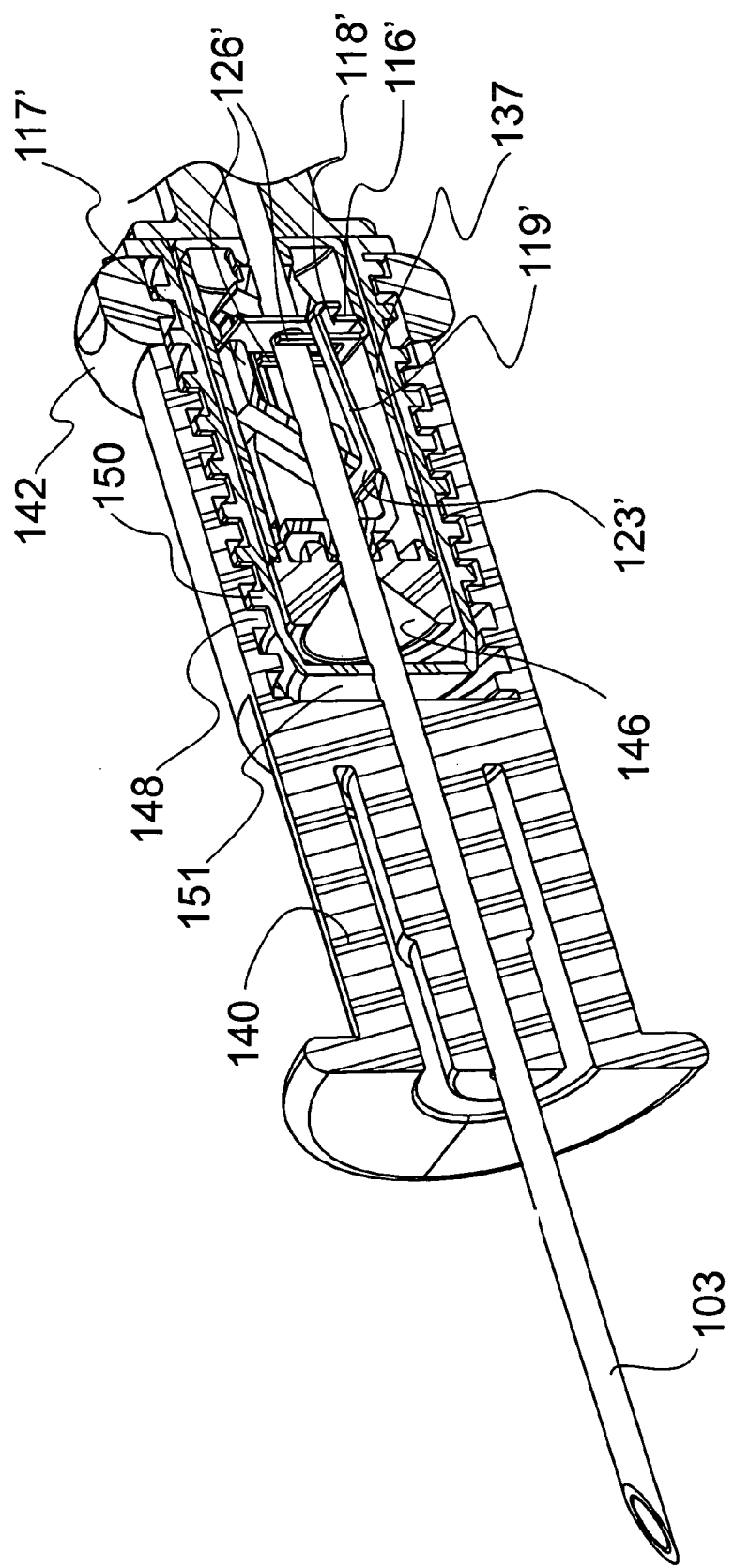
FIG. 17 is an enlarged cross-sectional view of the depth stop assembly shown in FIG. 16.
Figure 18:
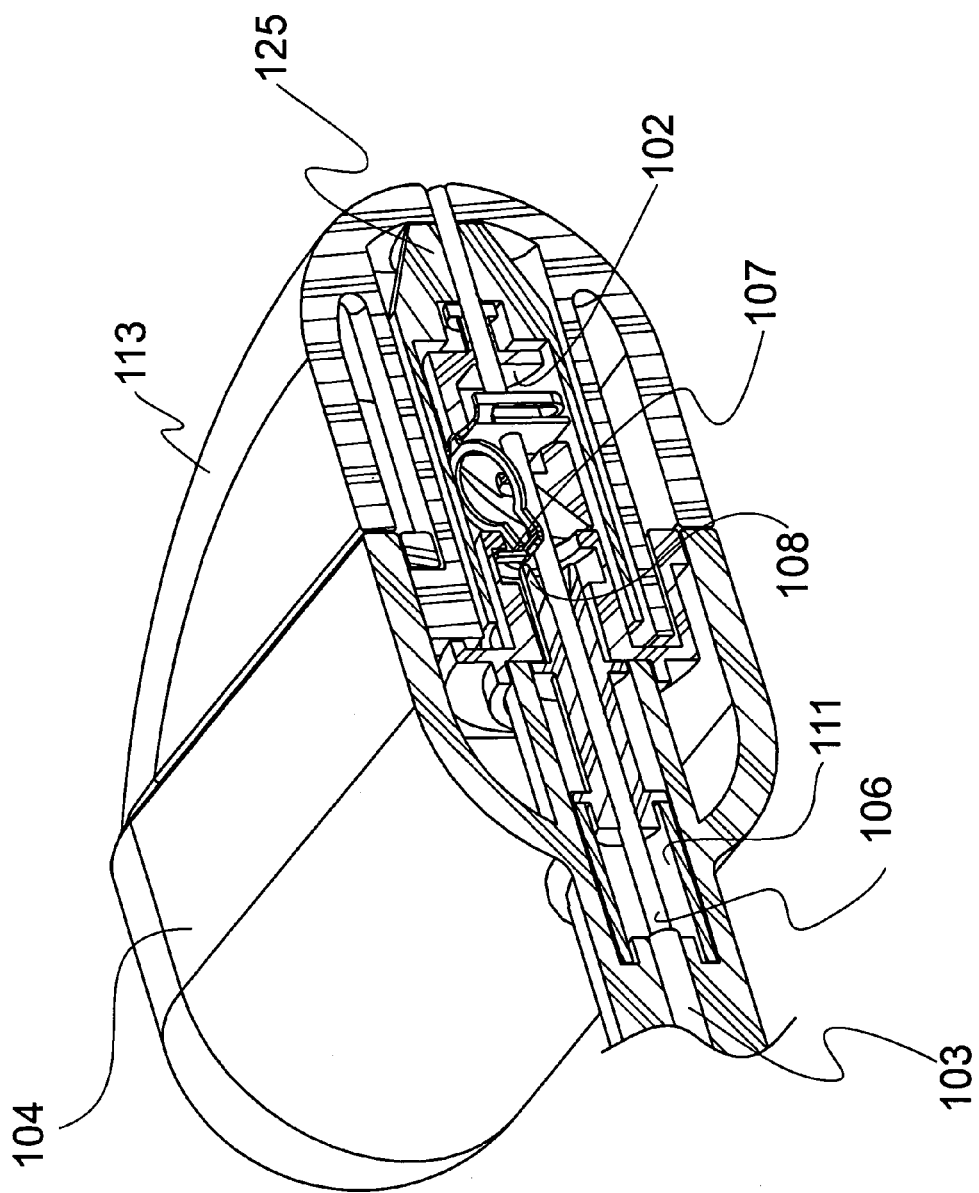
FIG. 18 is an enlarged cross-sectional view of the handle assembly shown in FIG. 16.
Figure 19:
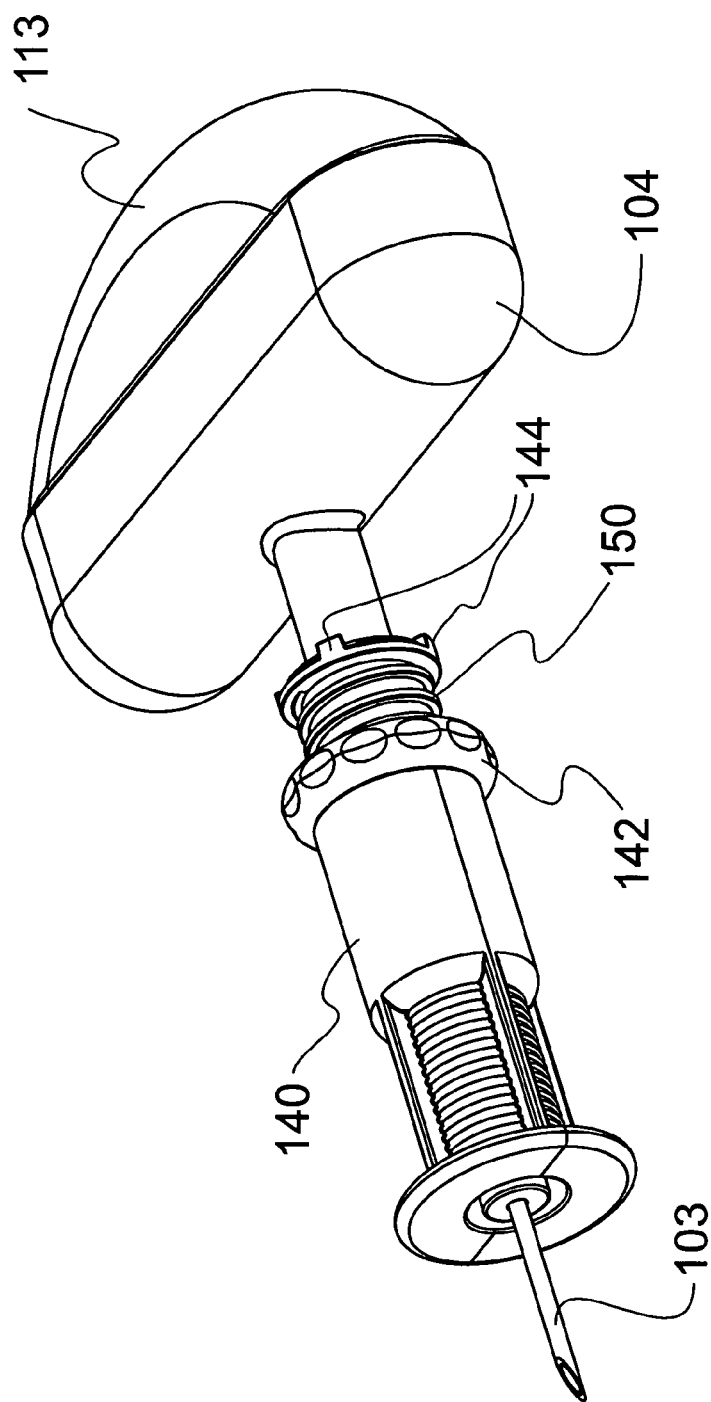
FIG. 19 is a perspective view of the medical needle shield apparatus shown in FIG. 16 with the depth stop assembly partially advanced along the threaded sleeve.
Figure 20:
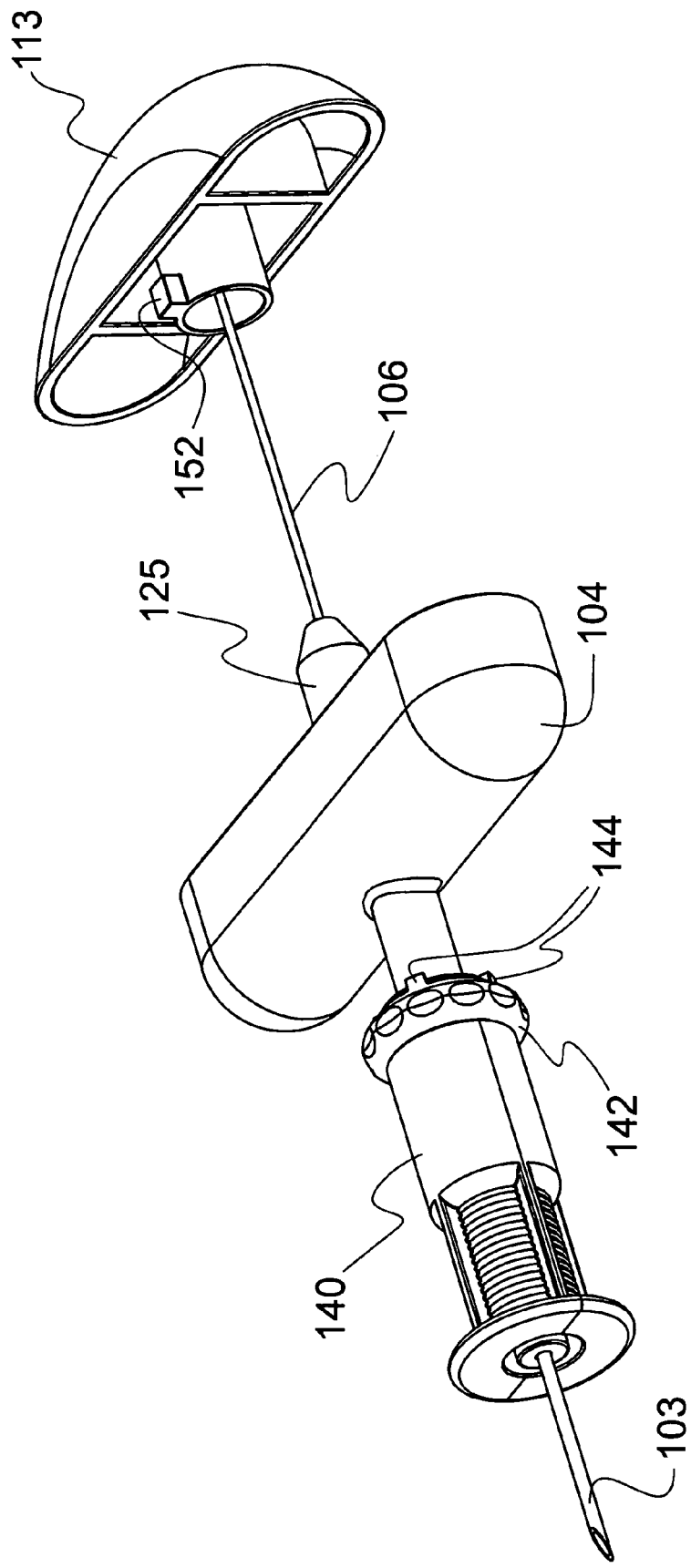
FIG. 20 is a perspective view of the medical needle shield apparatus shown in FIG. 16 with the stylet partially extended from the needle hub.
Figure 21:
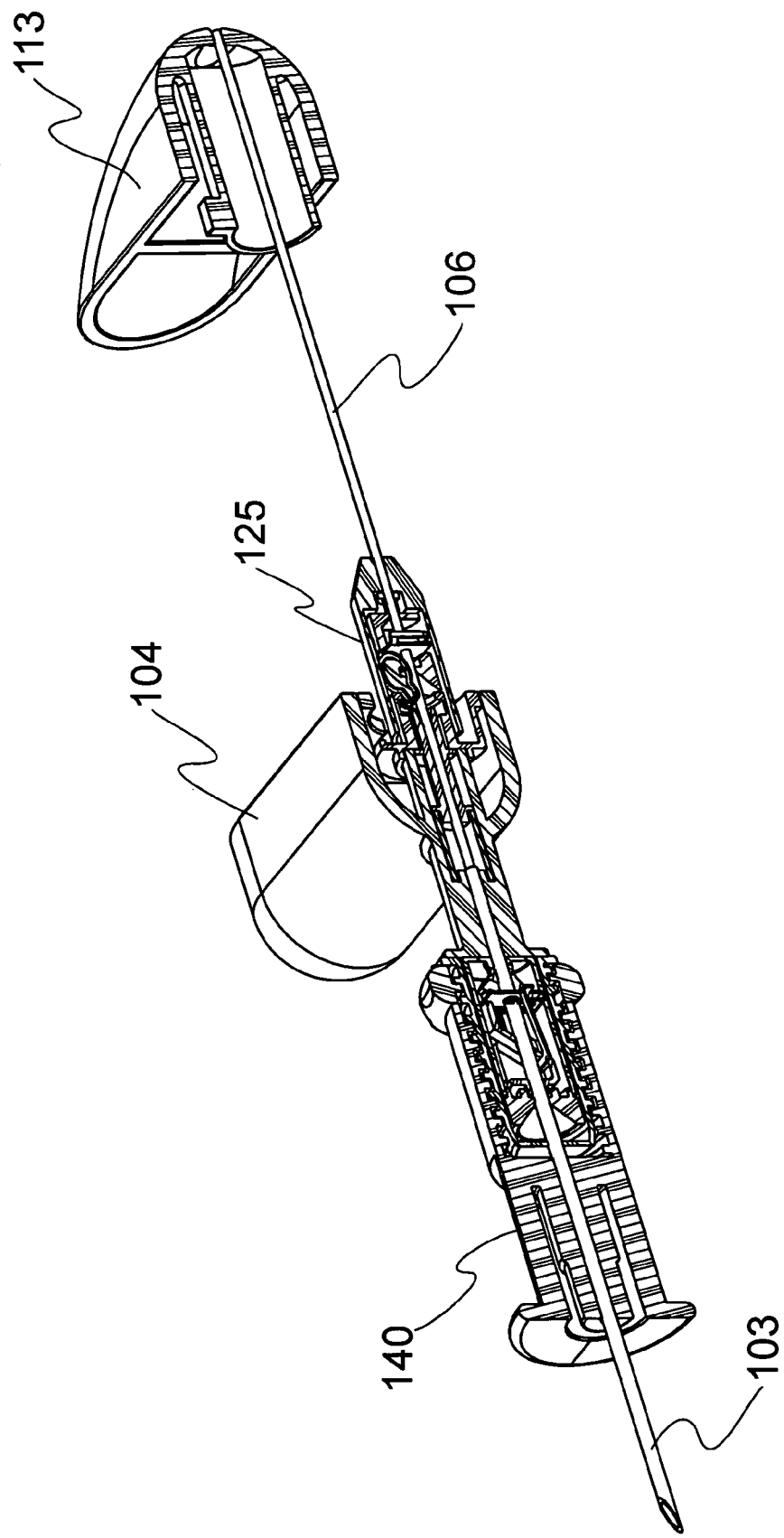
FIG. 21 is a cross-sectional view of the medical needle shield apparatus as shown in FIG. 20.

A needle shield 137 may be disposed in depth stop assembly 140 as illustrated in FIG. 17. Corresponding threads 148 and 150 disposed on depth stop assembly 140 and sleeve 151, respectively, provide for threadable movement of depth stop assembly 140. Needle shield 137 operates in similar fashion to shield 101 described in FIGS. 1–11, as will be discussed in more detail hereafter.

The medical needle shield apparatus for stylet 106 includes a binding member 105 that is disposed within a stylet shield 125, similar to that described with regard to FIGS. 1–11, that is extensible from a retracted position to an extended position to enclose a distal end of a stylet 106 of a needle assembly. Stylet 106 is slideably and concentrically disposed with a needle 103 of the needle assembly for employment therewith during a bone biopsy needle application. A stylet handle 113 is connected to stylet 106.

In operation, the clinician (not shown) manipulates handle 113 such that shield 101 is in the retracted position (FIGS. 16, 18, 19) and binding member 105 is in a non-binding or sliding position. Handle 113 may include a tab 152 for temporary securement to hub 104. Hub 104 includes an opening (not shown) such that handle 113 may be released from temporary securement as tab 152 is rotated to align tab 152 with the opening. Stylet 106 is extended relative to shield 101 such that needle hub 104 is disposed about needle 103 and needle hub 104 is releasably mounted with bearing 102. A procedure employing the medical needle shield apparatus with stylet 106 and needle 103 is performed by the clinician to completion.

Figure 22:
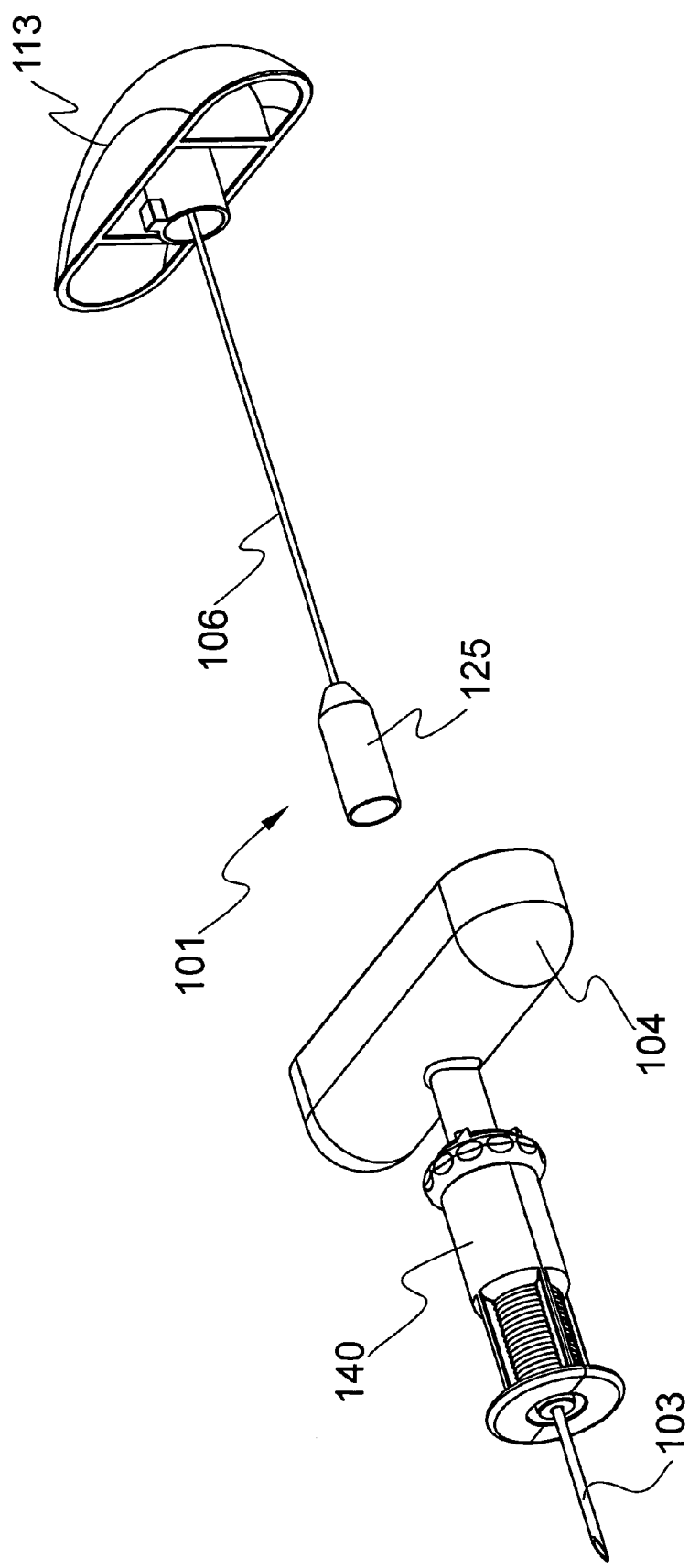
FIG. 22 is a perspective view of the medical needle shield apparatus shown in FIG. 16 with the stylet fully extended from the needle hub.

Needle hub 104 is releasably mounted with stylet handle 113. Referring to FIG. 22, stylet 106 is retracted proximally such that shield 101 is extended to the extended position and binding member 105 is disposed in a binding position. Needle hub 104 is released from stylet shield 125 in the extended position. This maintains stylet 106 within stylet shield 125 to avoid hazardous exposure to the distal end of stylet 106.

To re-access the stylet distal end 115 using the resettable passive safety device, the stylet shield 125 is brought to mate concentrically with the proximal end of the needle hub 104, in a similar fashion to the pre-activated state of the device. As this occurs, the binding member reset surface 107 comes into contact with the hub reset surface 108. This action is depicted in the embodiment shown in FIG. 23A.

As the stylet 106 is advanced from a proximal-to-distal direction, the hub reset surface 108 deflects the binding member reset surface 107, along with the end sensing member 119, to a position above the stylet 106 surface and urges the binding member 105 from the binding orientation to the sliding orientation. With the binding member 105 in the sliding orientation, the stylet 106 becomes free to advance into the needle 103.

Concurrently, due to the contact between the hub reset surface 108 and the binding member reset surface 107, the hub retainer 114 is urged into the hub slot 124. This causes the hub retainer 114 of the binding member 105 to again retain the needle hub 104 to the safety shield 101 through the interaction with the hub slot 124.

Figure 16:
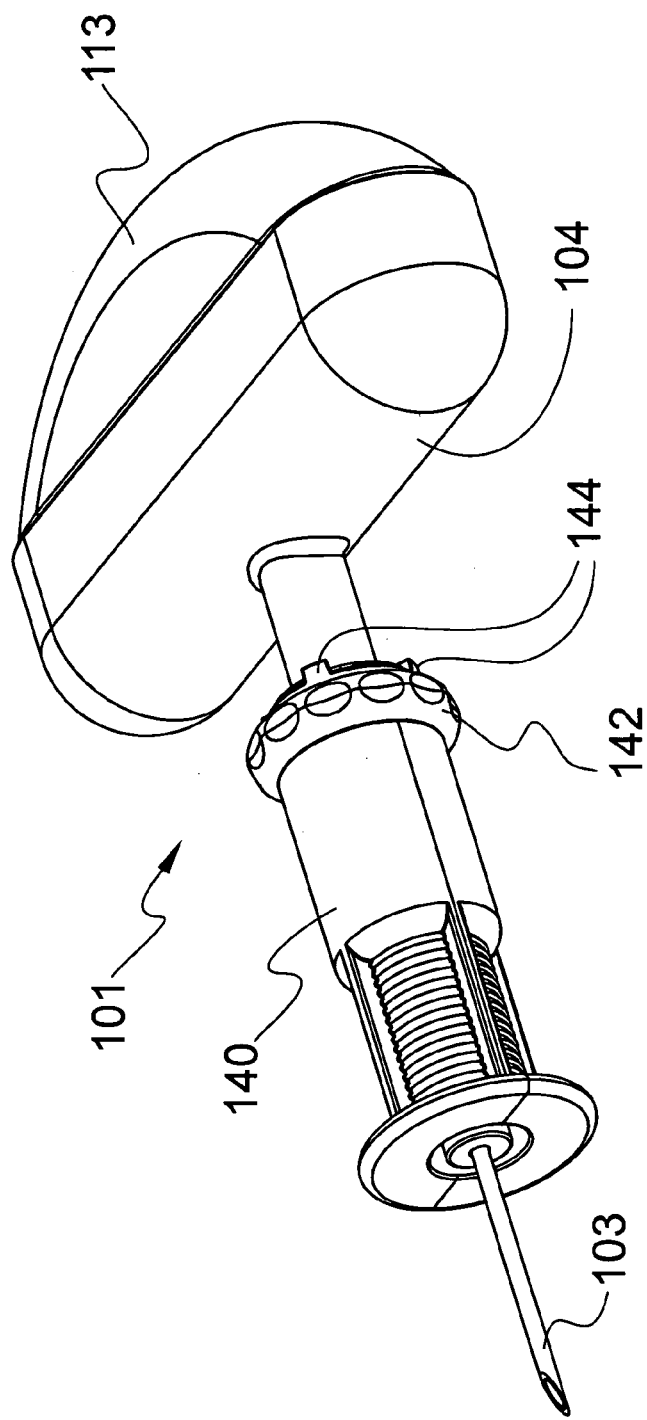
FIG. 16 is a perspective view of an embodiment of a medical needle shield apparatus adapted for use with a bone biopsy needle in accordance with the principles of the present disclosure.

Upon being reset, the stylet shield 125 and needle 103 are positioned over the stylet 106, as seen in FIG. 16. During the medical procedure, the style 106 will be automatically protected by the stylet shield 125 as the stylet 106 is again withdrawn from the needle.

Figure 24:
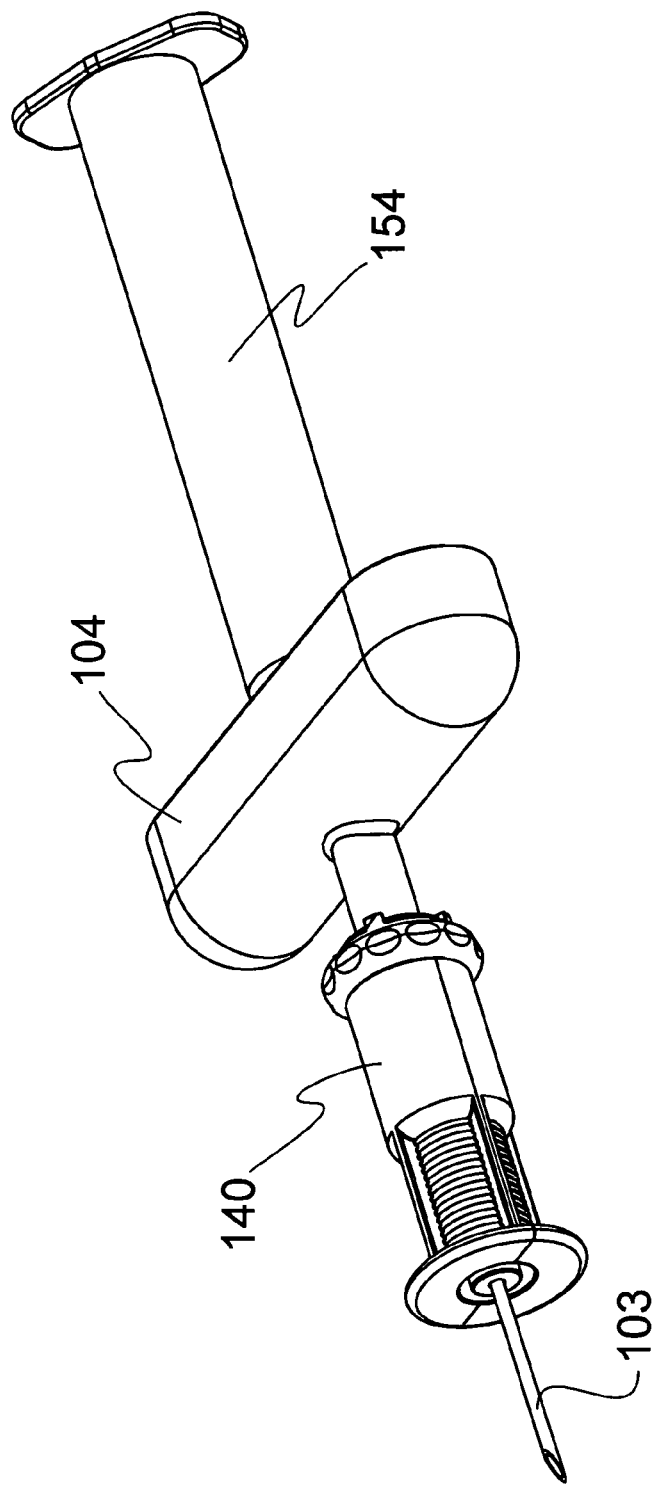
FIG. 24 is a perspective view of the medical needle shield apparatus shown in FIG. 16 with the stylet removed and a syringe inserted in the needle hub for aspiration purposes.

FIG. 24 illustrates a syringe inserted into hub 104 for aspiration purposes with stylet 106 removed.

Figure 25:
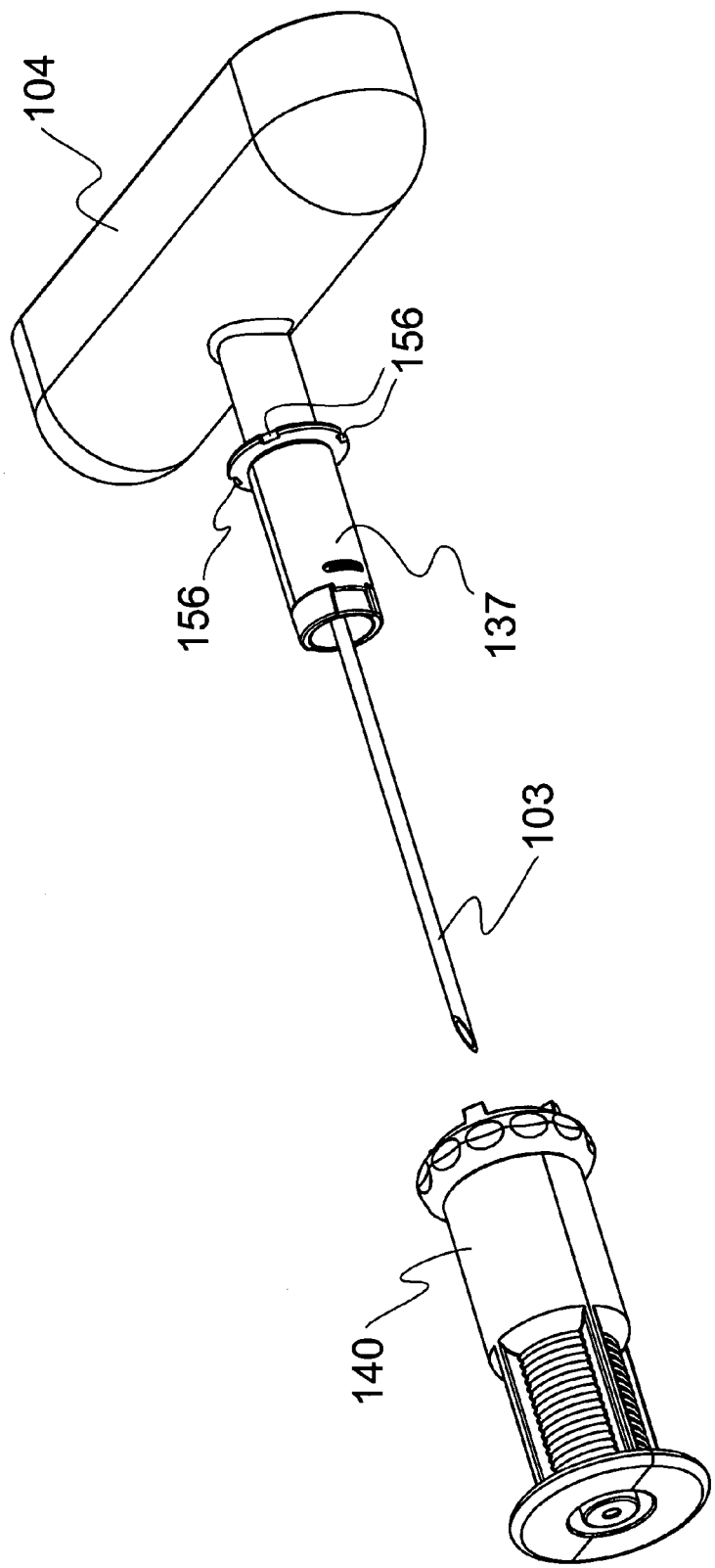
FIG. 25 is a perspective view of the medical needle shield apparatus shown in FIG. 16 with the depth stop assembly removed.
Figure 26:
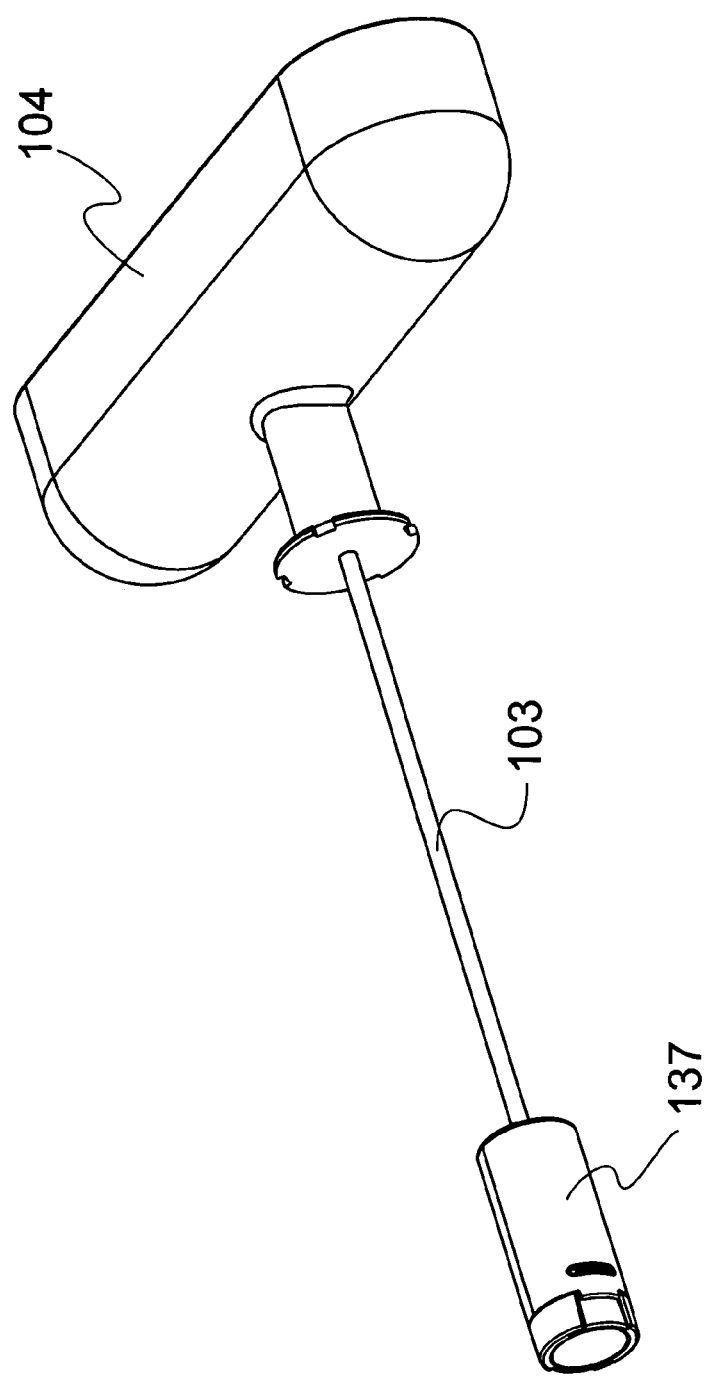
FIG. 26 is a perspective view of the medical needle shield apparatus shown in FIG. 16 in the shielded configuration.
Figure 27:
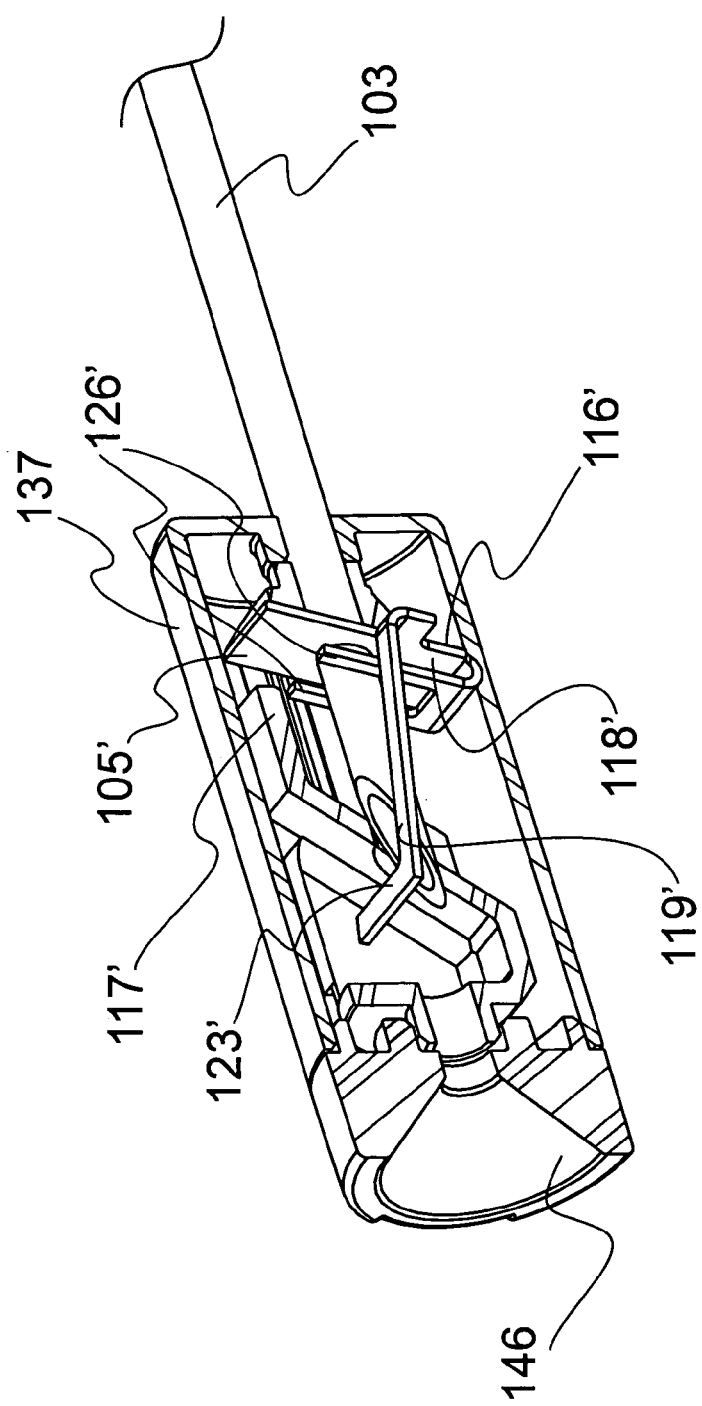
FIG. 27 is an enlarged cross-sectional view of the medical needle shield apparatus shown in FIG. 26.

FIG. 25 illustrates the resettable safety shield device 101 with the depth stop assembly 140 removed and the needle shield 137 in the retracted position. FIGS. 26–27 show the needle shield 137 in the shielded configuration. A binding member 105' is disposed within needle shield 137 and defines binding surfaces (not shown). Binding surfaces form an aperture configured for slidable receipt of hollow needle 103 between the retracted position and the extended position. Binding member 105' includes a drag inducing member, such as, for example, friction members 126' extending therefrom. Binding member 105' has a needle communicating surface 123' that is engageable with hollow needle 103 to prevent rotation of binding member 105'.

Friction members 126' are configured for slidable engagement with hollow needle 103 between the retracted position and the extended position such that friction members 126' engage hollow needle 103 to create a drag force with hollow needle 103. It is envisioned that one or a plurality of friction members 126' may be employed.

The drag force in conjunction with one of blocking members 116' and/or 117', cause binding member 105' to move to a binding position (FIG. 27). The force created by blocking members 116' and/or 117' acts in a direction opposite to the drag force. This causes a force couple, which moves binding member 105' to the binding position.

A funnel portion 146 in needle shield 137 acts as a probe guide to facilitate insertion of a shepherd's hook or the like. Depth stop 140 may be slideably removed with safety shield 137 remaining in the proximal position. This allows a clinician to utilize the entire length of needle 103. As shown, depth stop 140 is removed prior to activation of safety shield 137. Alternatively, safety shield 137 may be connect to, or formed as part of, the depth stop 140.

Figure 28:
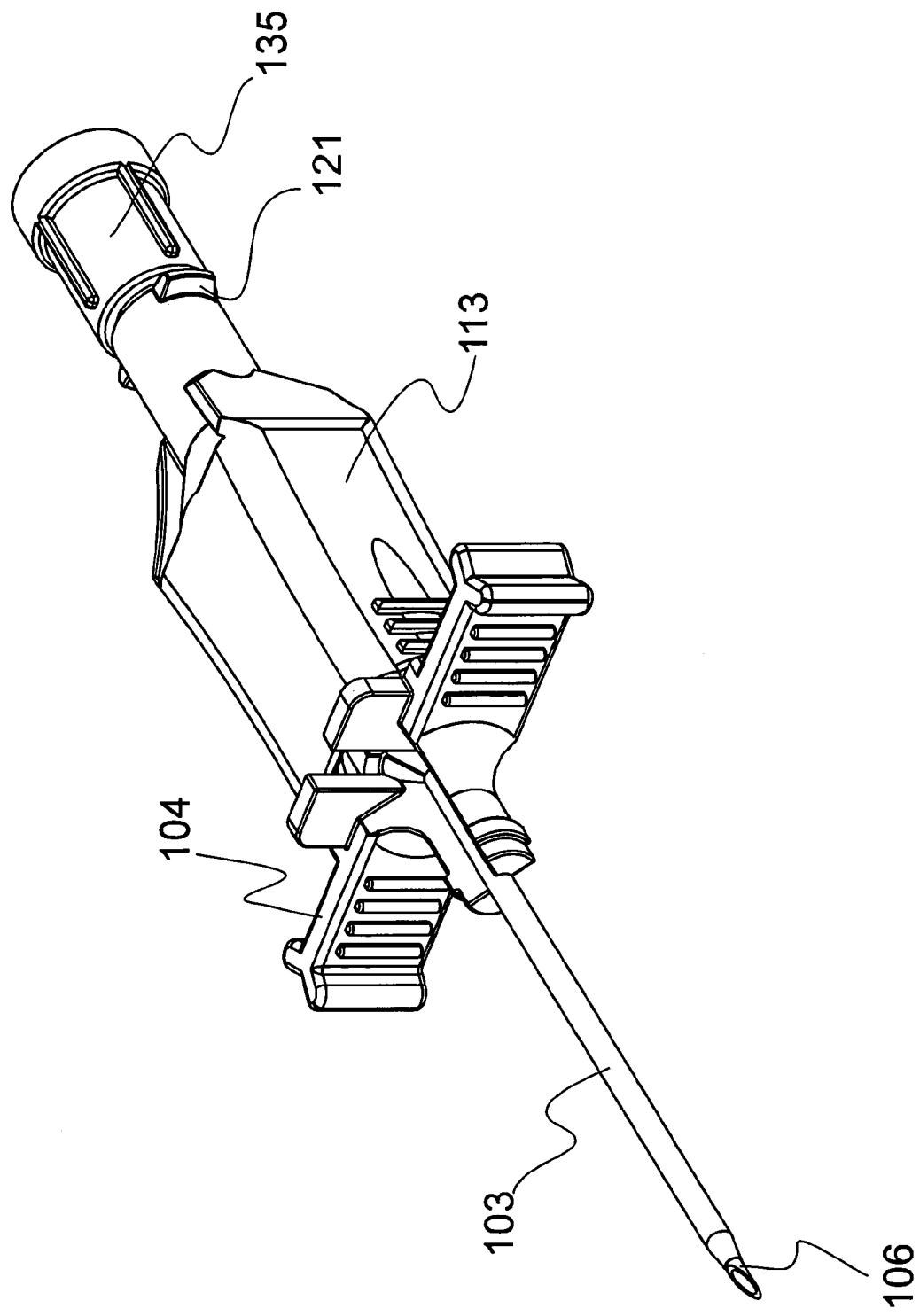
FIG. 28 is a perspective view of an embodiment of a medical needle shield apparatus adapted for use with a PICC introducer in accordance with the principles of the present disclosure.
Figure 29:
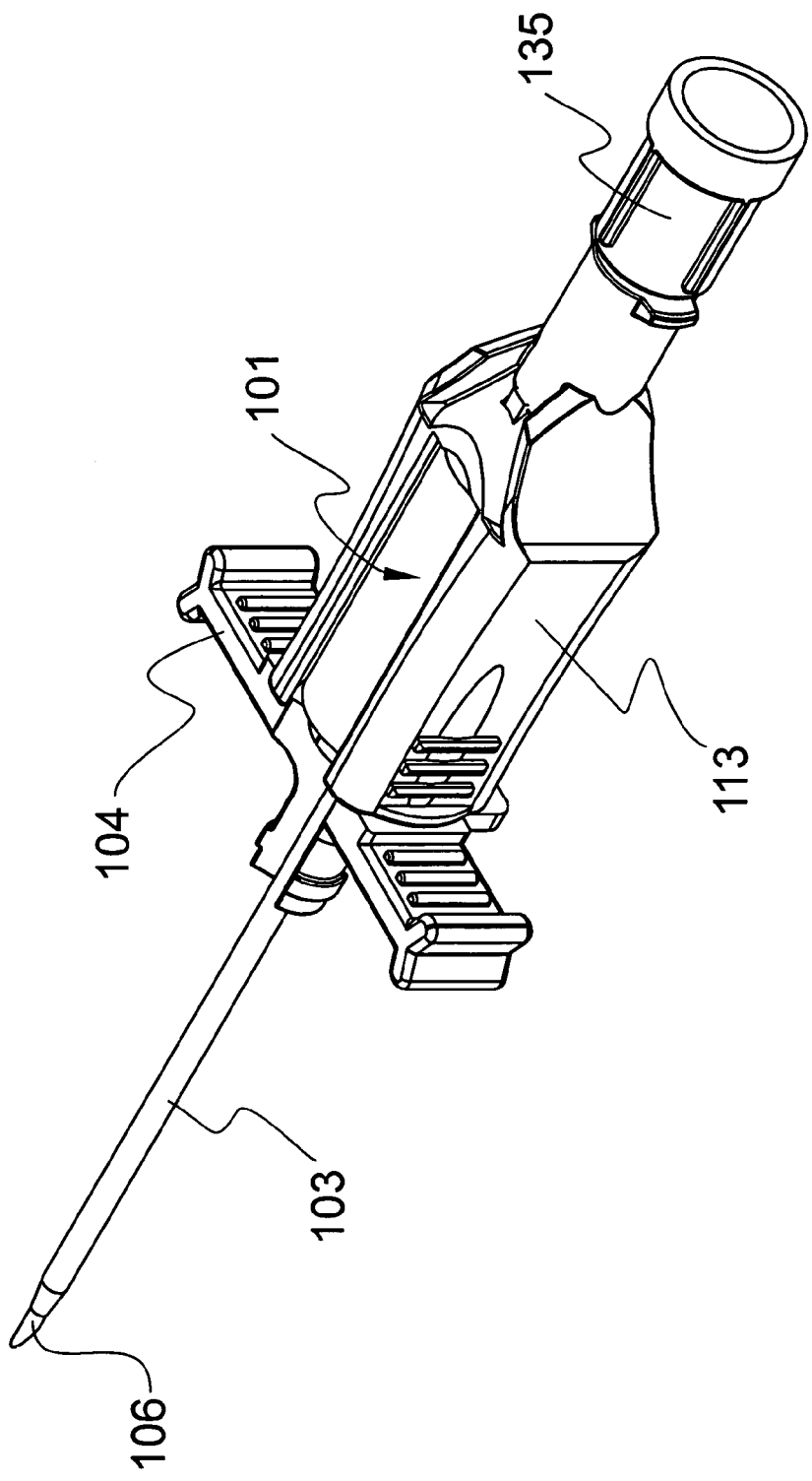
FIG. 29 is an alternative perspective view of an embodiment of a medical needle shield apparatus illustrated in FIG. 28.

FIGS. 28–29 illustrate the resettable safety shield device according to the present disclosure as applied to a PICC introducer or similar catheter and needle introducers. In this embodiment, the hollow needle 103 is polymeric, and the stylet (or inner needle) 106 is a sharp, hollow bore cannula. The handle 113 of the PICC Introducer has a flash plug 135 and a flash chamber 136 that is in communication with inner needle 106. A luer fitting 121 communicates with the flash chamber 136 and allows the fitting of other medical devices.

Figure 31:
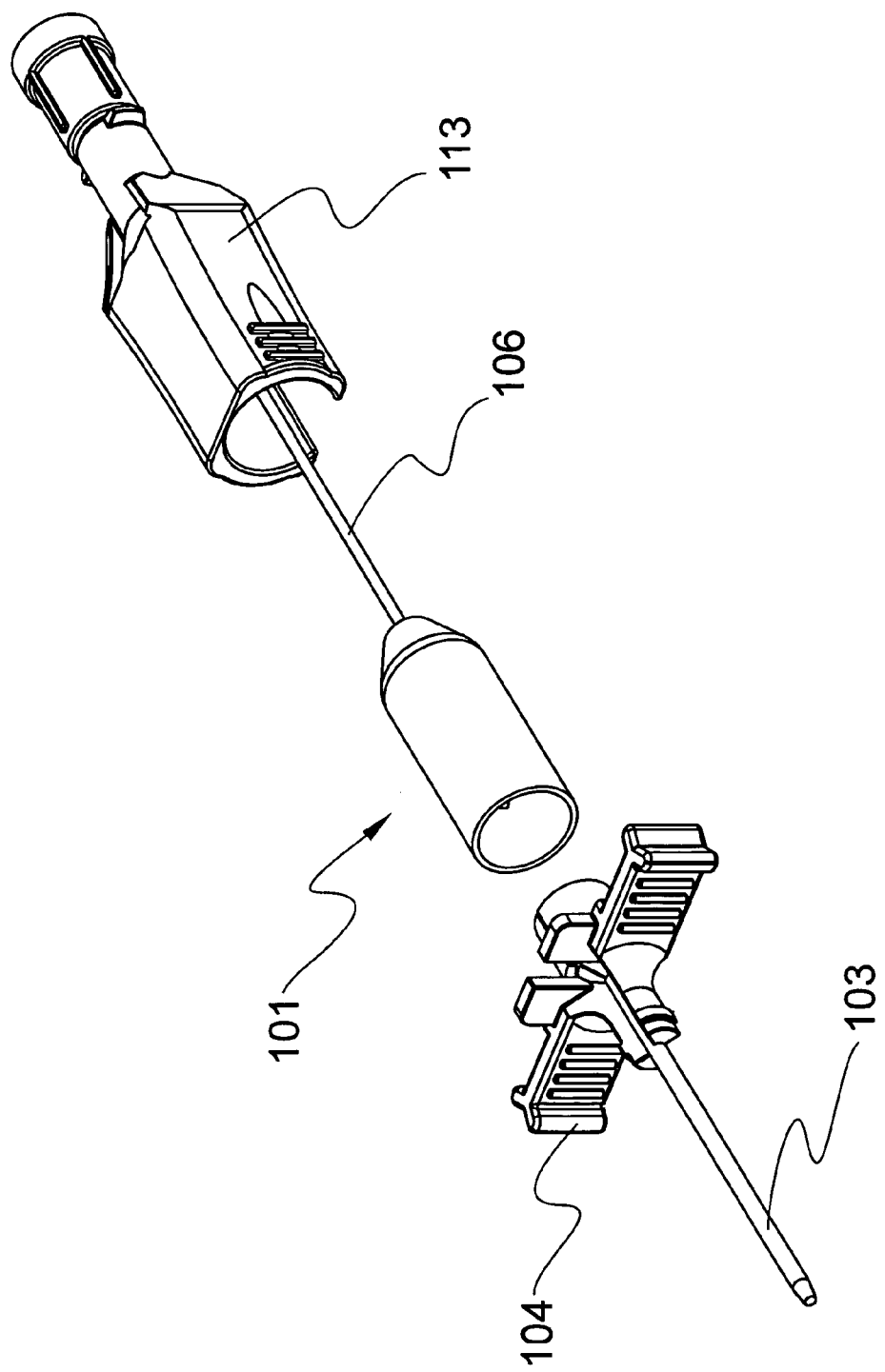
FIG. 31 is a perspective view of the embodiment shown in FIG. 28 in a shielded configuration.
Figure 32:
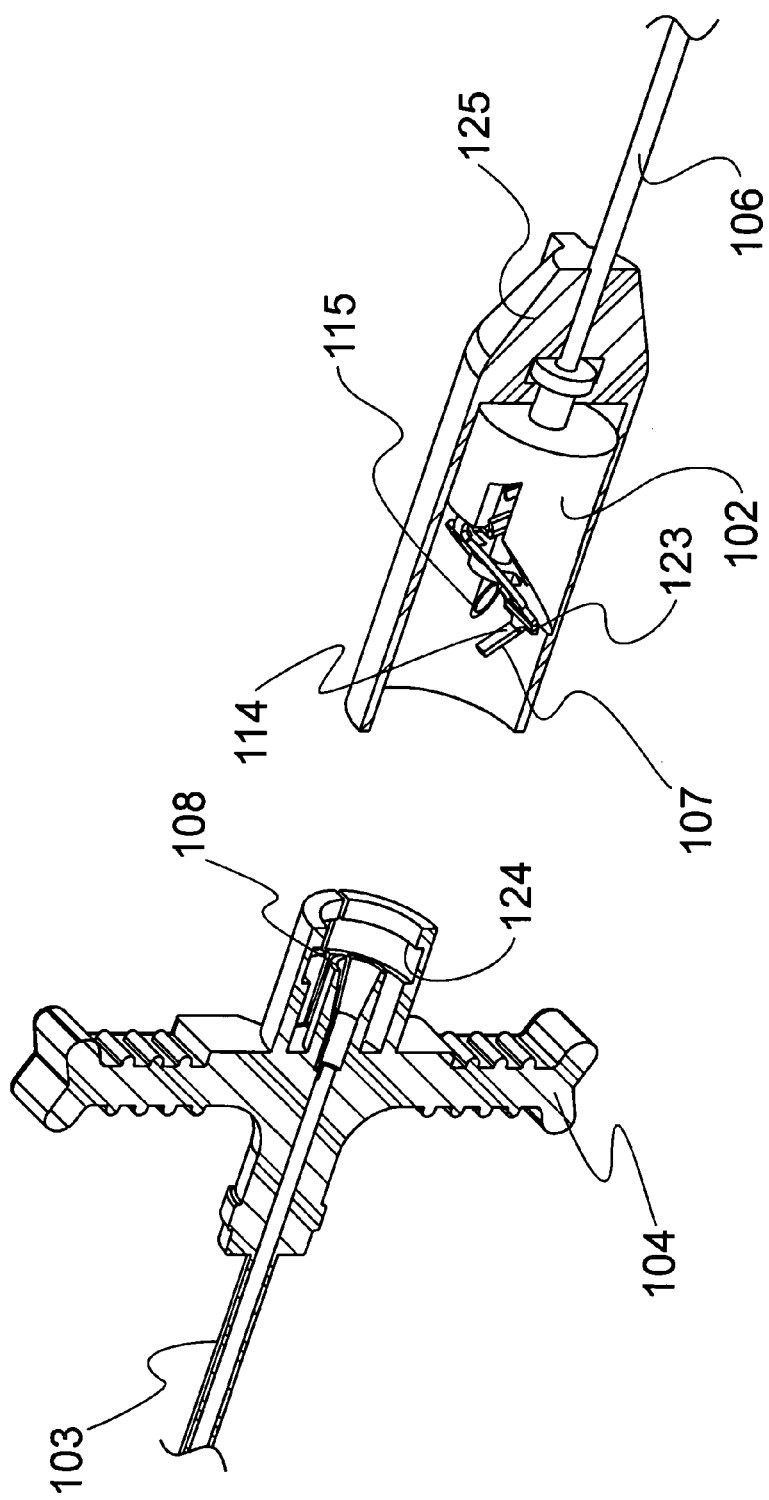
FIG. 32 is a cutaway perspective view of the embodiment shown in FIG. 28 in a shielded configuration.

The medical needle shield apparatus includes a shield 101, similar to those described, that is extensible from a retracted position (FIG. 28) to an extended position (FIGS. 31–32) to enclose a distal end of hollow needle 103 of a needle assembly. Hollow needle 103 is slideably and concentrically disposed with a hub 104 (FIG. 28) of the needle assembly for employment therewith during a PICC introducer application. Hub 104 may, or may not, be splitable. Hub 104 is desirably fabricated from a polymeric material. It is contemplated that the medical needles of the present disclosure may incorporate a protective needle sheath member to facilitate additional protection during transportation and use of the medical needles.

A handle 113 is connected to inner needle 106. Handle 113 may have a flash chamber 139 in communication with inner needle 106. A luer fitting 121 communicates with flash chamber 139 that facilitates connection to various medical devices via either a luer slip or luer lock attachment feature.

A binding member 105, similar to that described with regard to FIGS. 1–11, is disposed within shield 101. Shield 101 includes a bearing 102 that houses binding member 105.

Needle hub 104 is mounted with hollow needle 103. Needle hub 104 is releasably mounted with shield 101 via releasable engagement with a retainer 114 of binding member 105. Needle hub 104 has a hub slot 124 for receipt and engagement with binding member 105. This configuration facilitates removal and use of hub 104 from shield 101 during a medical needle application.

A flange of needle hub 104 is concentrically supported by a control surface of a stylet shield 125, discussed below. The control surface engages the flange for releasable support thereof. Retainer 114 extends for receipt within a hub slot 124 of needle hub 104. In association with a non-binding or sliding orientation of binding member 105, retainer 114 is disposed within hub slot 124 for releasably mounting with shield 101. As inner needle 106 is retracted and shield 101 is extended, retainer 114 rotates in a counter clockwise direction and disengages from hub slot 124 to release needle hub 104 from stylet shield 125.

A stylet shield 125 is disposed for rotation and enclosure of the distal end of inner needle 106. Stylet shield 125 is mounted with handle 113 and freely rotates relative to shield 101 and inner needle 106 in the extended position of shield 101. Relative rotation of stylet shield 125 is facilitated by support at bearing openings formed in stylet shield 125 and axles, similar to those described above. In a binding position, the bearing configuration supports rotation of stylet shield 125 relative to shield 101 and inner needle 106.

Inner needle 106 is retracted proximally such that shield 101 is extended to the extended position and binding member 105 is disposed in a binding position. Needle hub 104 is released from shield 101 and shield 101 encloses the distal end of needle 103 in the extended position. This maintains needle 103 within shield 101 to avoid hazardous exposure to the distal end of needle 103.

In operation, needle hub 104 is released from shield 101 and a stylet shield 125 encloses the distal end of inner needle 106 in the extended position, as described above. This maintains inner needle 106 within shield 101 to avoid hazardous exposure to the distal end thereof.

Figure 30:
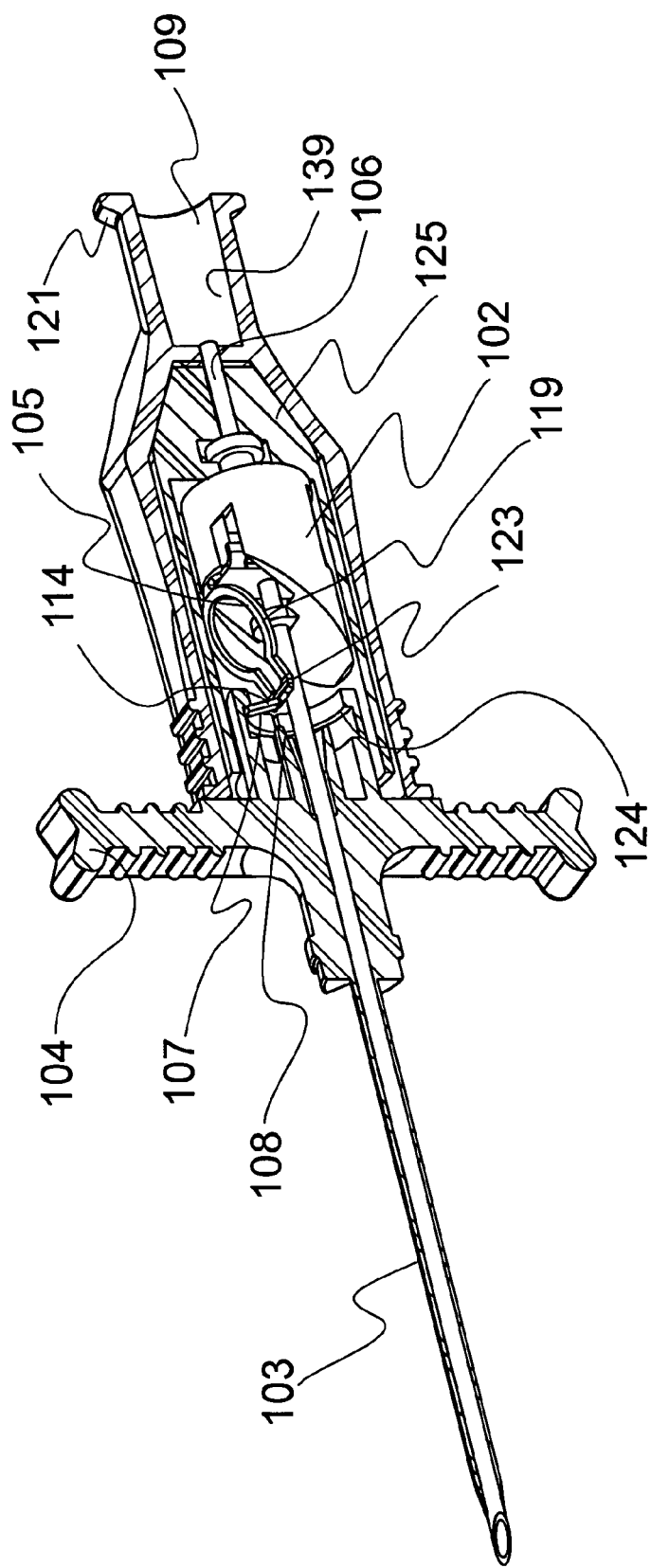
FIG. 30 is an enlarged cutaway perspective view of the embodiment shown in FIG. 28 in a retracted position.
Figure 33:
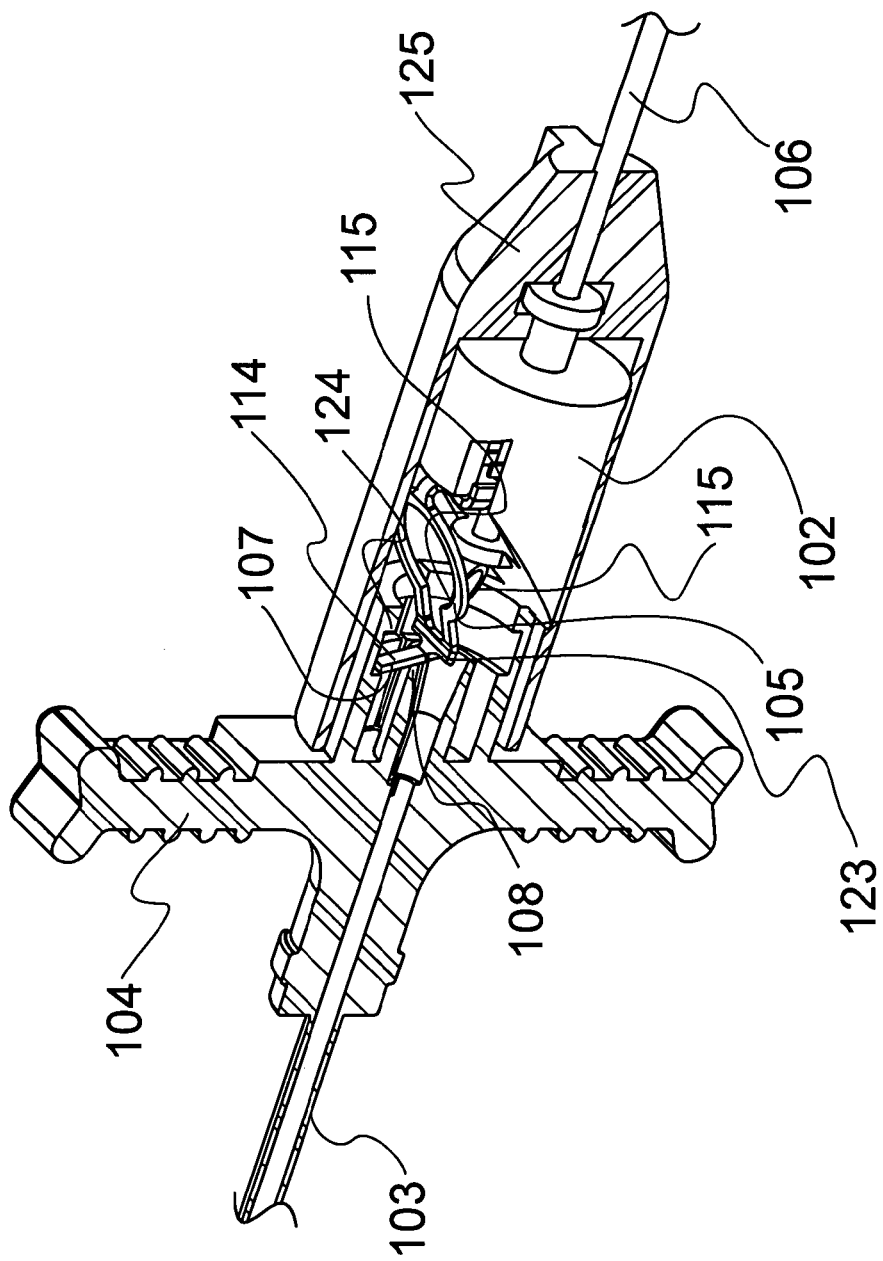
FIG. 33 is a cutaway perspective view of the embodiment shown in FIG. 28 in a reset configuration in accordance with the present disclosure.
Figure 34:
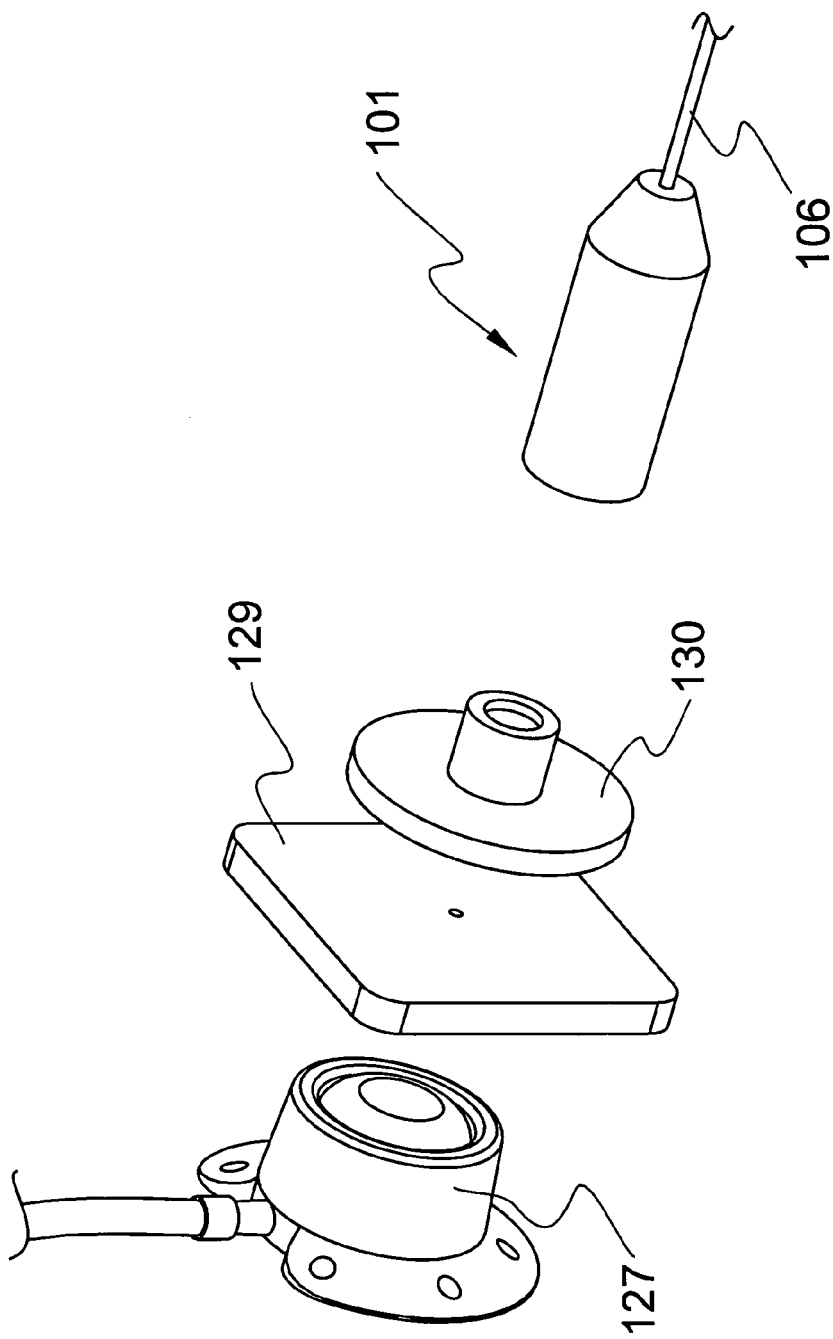
FIG. 34 is a perspective view of an embodiment of a medical needle shield apparatus adapted for use with an implanted port access in accordance with the principles of the present disclosure.
Figure 35:
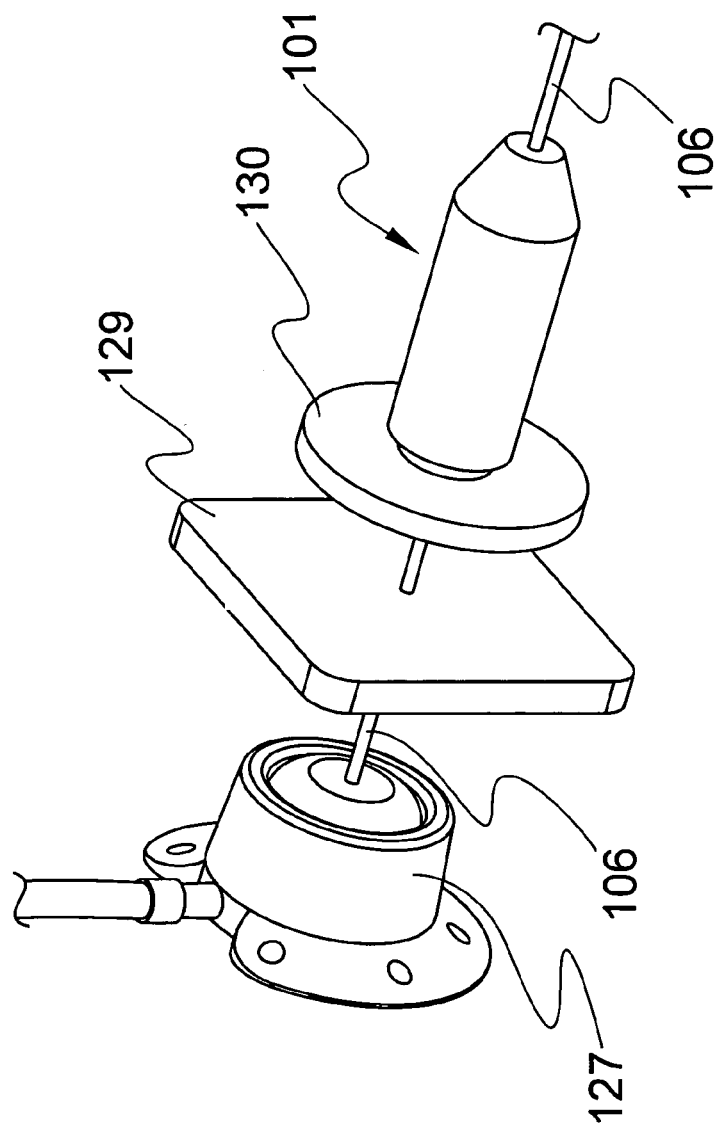
FIG. 35 is a perspective view of the embodiment shown in FIG. 34 in an unshielded configuration.
Figure 36:
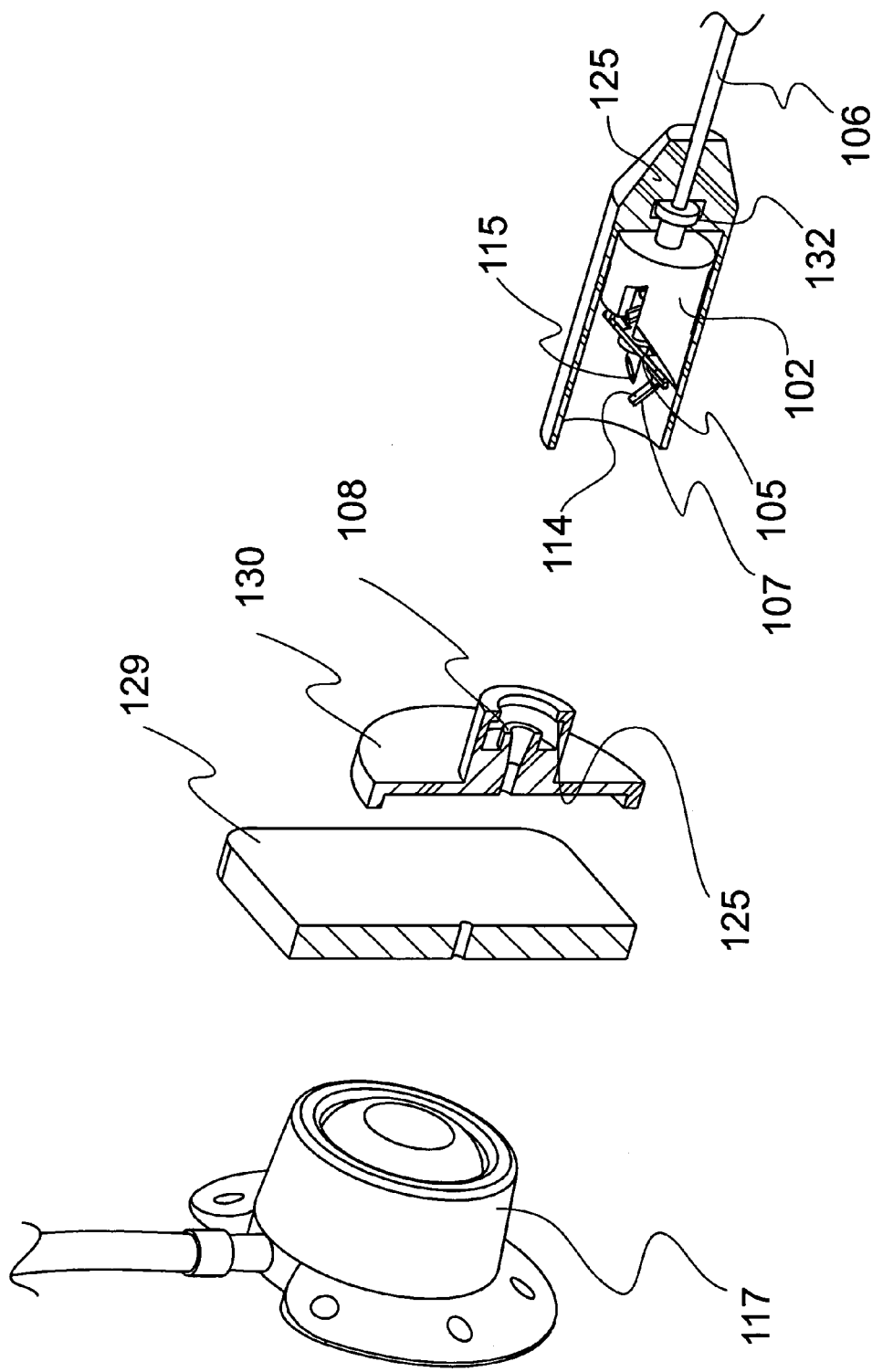
FIG. 36 is a cutaway perspective view of the embodiment shown in FIG. 34 in a shielded configuration.
Figure 37:
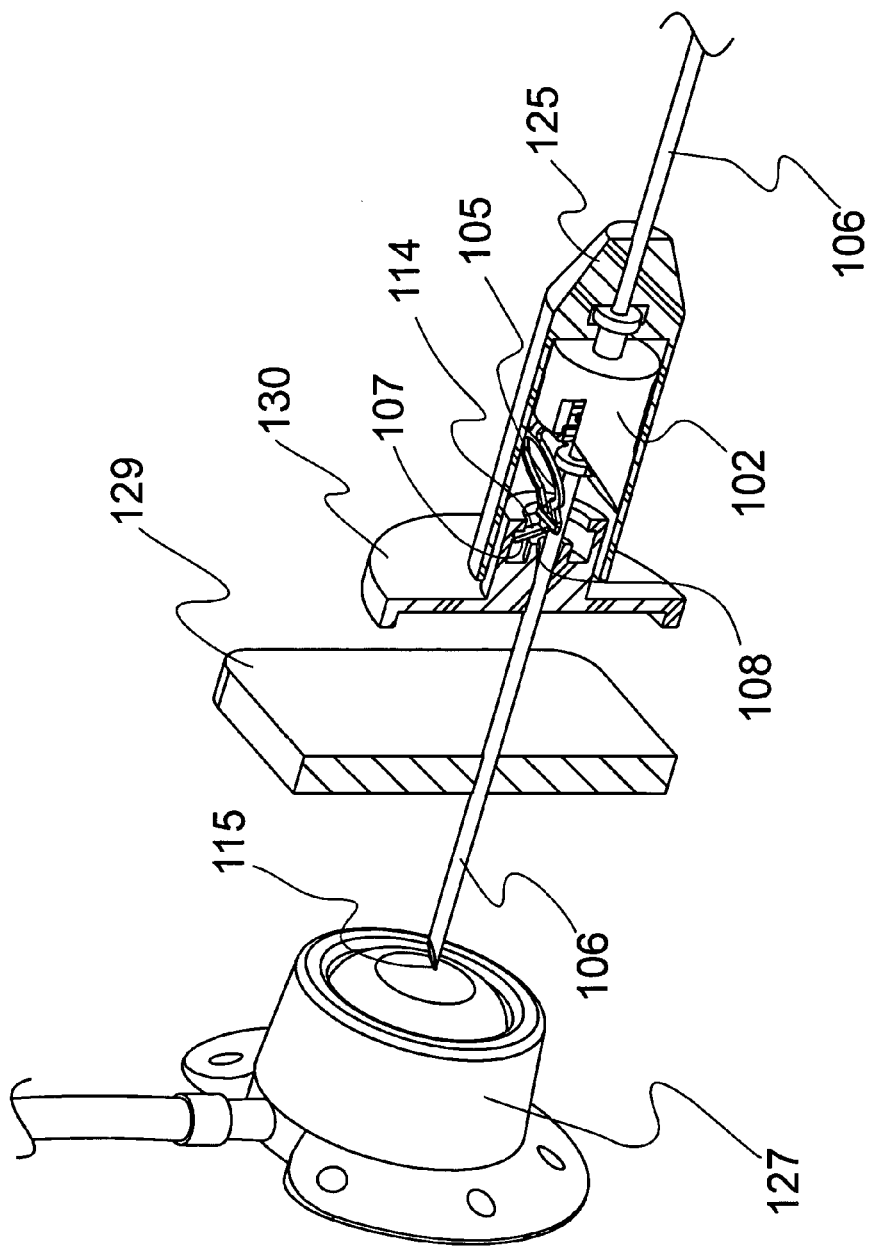
FIG. 37 is a cutaway perspective view of the embodiment shown in FIG. 34 in an unshielded configuration.
Figure 38:
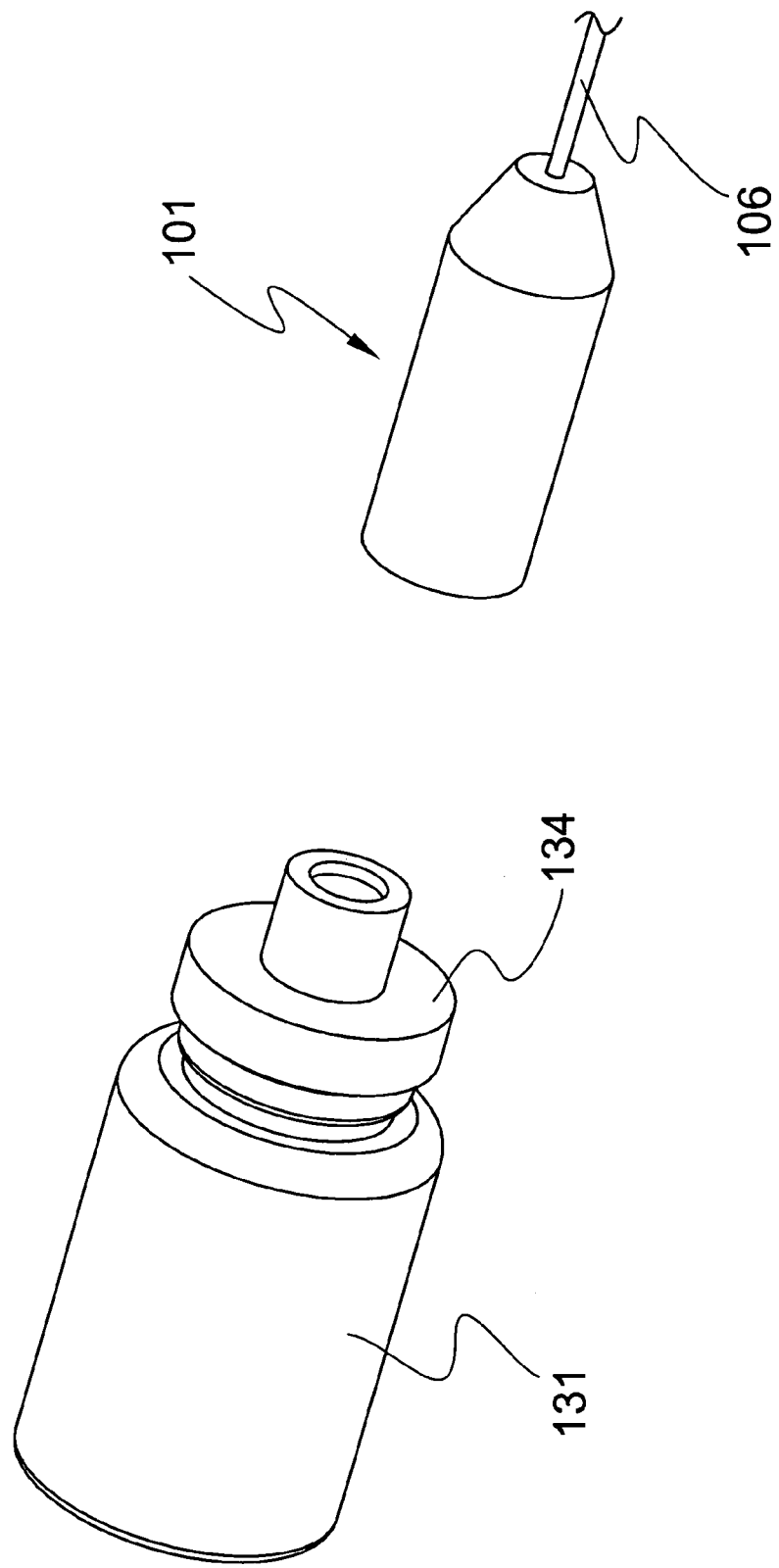
FIG. 38 is a perspective view of an embodiment of a medical needle shield apparatus adapted for use with a drug vial access in accordance with the principles of the present disclosure.
Figure 39:
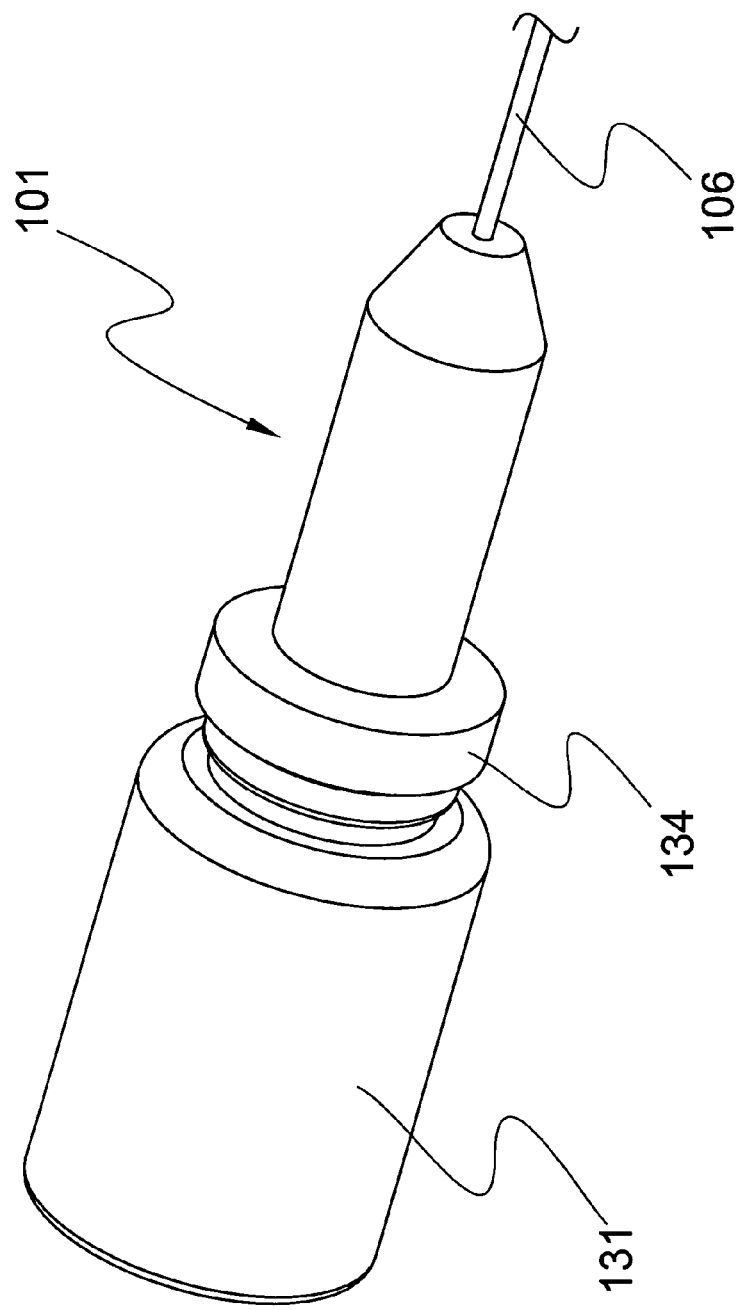
FIG. 39 is a perspective view of the embodiment shown in FIG. 38 in an unshielded configuration.
Figure 40:
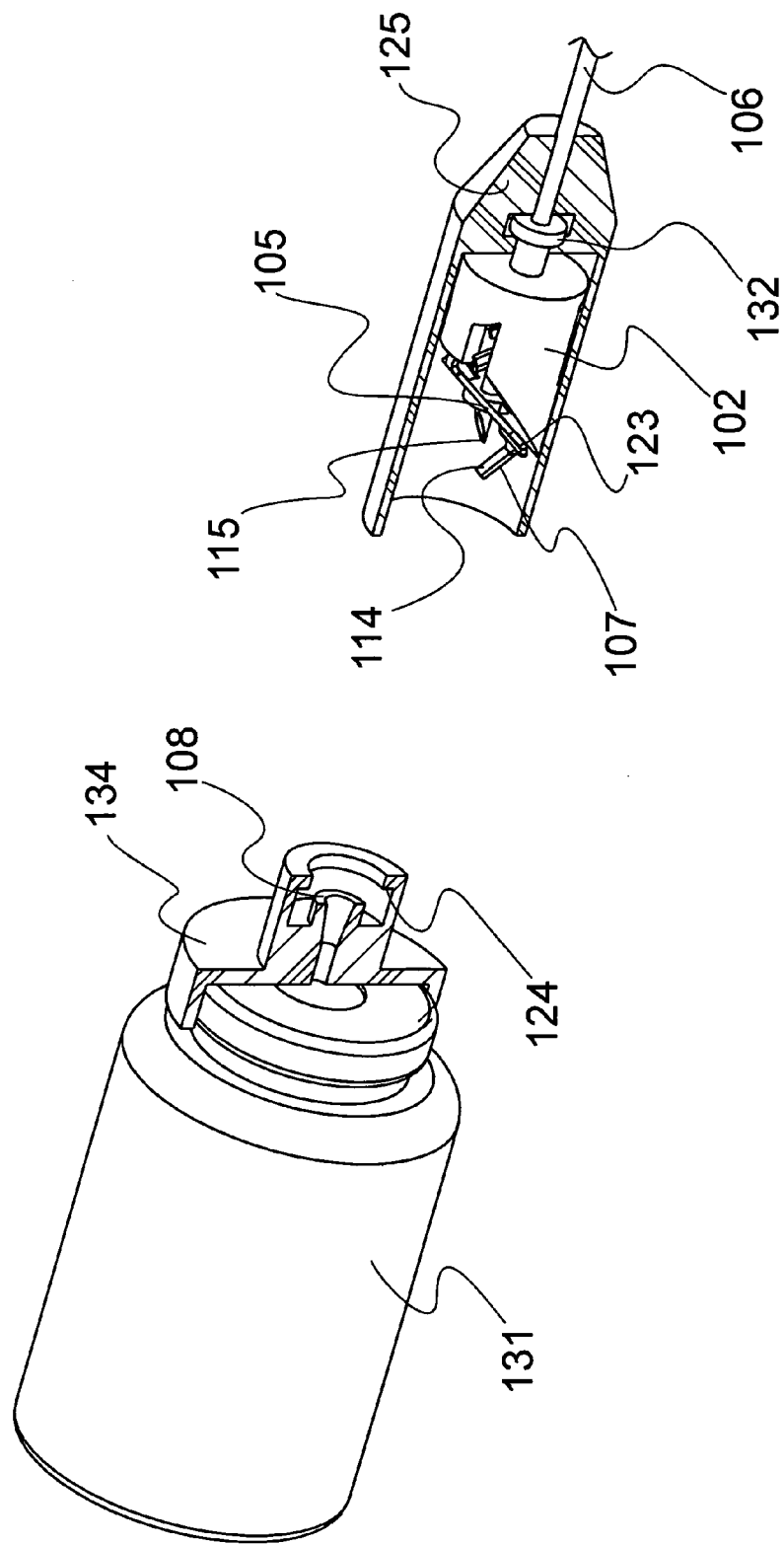
FIG. 40 is cutaway perspective view of the embodiment shown in FIG. 39 in a shielded configuration.
Figure 41:
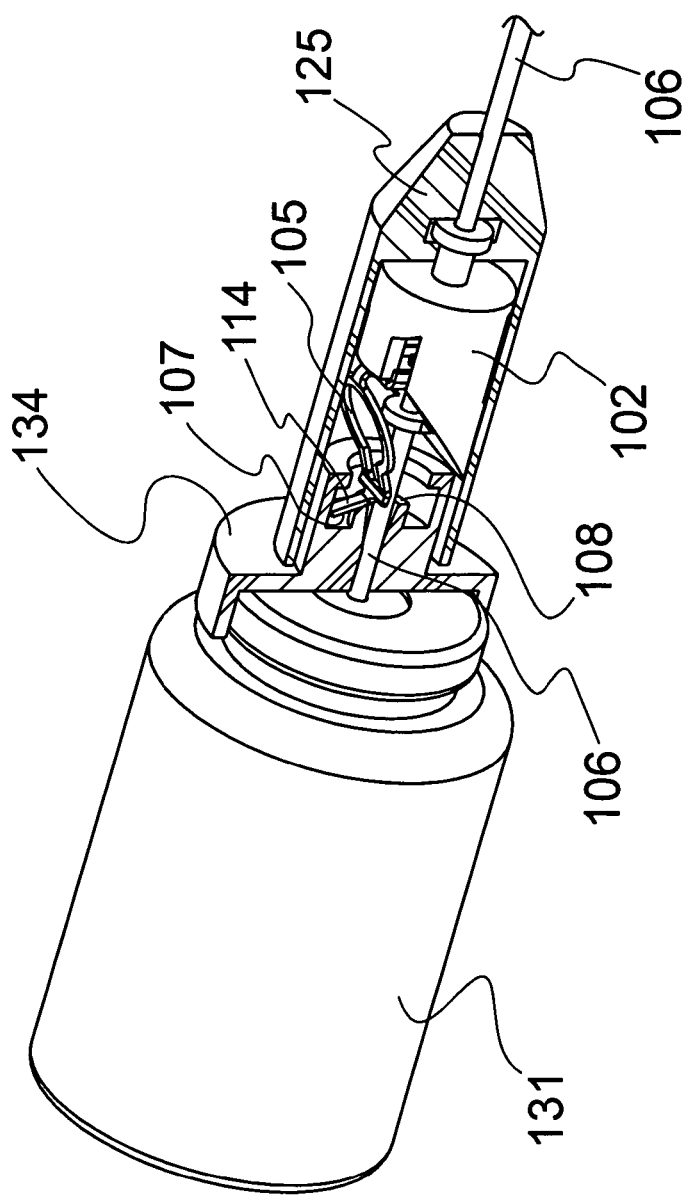
FIG. 41 is a cutaway perspective view of the embodiment shown in FIG. 39 in a reset configuration according to the principles of the present disclosure.

To re-access the inner needle 106 using the resettable passive safety device, the stylet shield 125 of the rotating focusing is brought to mate concentrically with the proximal end of the needle hub 104, in a similar fashion to the pre-activated state of the device. As this occurs, the binding member reset surface 107, on the end sensing member 119, comes into contact with the hub reset surface 108. This action is depicted in the embodiment shown in FIGS. 30 and 33.

As the inner needle 106 is advanced from a proximal-to-distal direction, the hub reset surface 108 deflects the binding member reset surface 107, along with the end sensing member 119, to a position above the inner needle 106 surface and urges the binding member 105 from the binding orientation to the sliding orientation. With the binding member 105 in the sliding orientation, the inner needle 106 becomes free to advance into hollow needle 103.

Concurrently, due to the contact between the hub reset surface 108 and the binding member reset surface 107, the hub retainer 114 is urged into the hub slot 124. This causes the hub retainer 114 of the binding member 105 to again retain the needle hub 104 to the safety shield 101 through the interaction with the hub slot 124.

Upon being reset, the safety shield 101 and hollow needle 103 are positioned over the inner needle 106, as seen in FIG. 28. During the medical procedure, the inner needle 106 will be automatically protected by the safety shield 101 as the inner needle 106 is again withdrawn from the needle.

FIGS. 34–37 illustrate the resettable safety shield device according to the present disclosure as applied to a port access device or implanted pump. It is contemplated herein that the port access device may be implanted or exterior to a patient. Operation and construction of this embodiment is in accordance with the various embodiments described herein such as for example the embodiments disclosed in FIGS. 1–11. FIGS. 34–37 show an implanted port 127 and skin layer 129 along with an implanted port access body 130. The port access body contains the hub reset surface 108. In the present embodiment, the stylet 106 is protected by the safety shield 101 before use. Hub reset surface 108 and binding member reset surface 107 reset the safety device as described hereinbefore to allow stylet 106 to pass through the skin layer 129 and enter the implanted port 127. The safety shield device reactivates upon removal of stylet 106 from the implanted port access body 130.

With reference to FIGS. 38–41, illustrated is a resettable safety shield device according to the present disclosure as applied to a drug vial access. Operation and construction of this embodiment is in accordance with the various embodiments described herein such as for example the embodiments disclosed in FIGS. 1–11. FIGS. 38–41 show a drug vial 131 along with a corresponding drug vial access body 134. Stylet 106 is protected by a safety shield 101 before use. Hub reset surface 108 engages binding member reset surface 107 to allow stylet 106 to enter drug vial 131. The safety device re-activates upon removal of stylet 106 from drug vial access body 134.

The invention of the present disclosure may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A medical needle shield apparatus comprising:
   a needle hub having an outer needle cannula extending therefrom to a distal end, an inner needle being disposed for slidable movement with the outer needle cannula; and
   at least one shield being extensible from a retracted position to an extended position to enclose a distal end of the inner needle,
   the shield including a binding member disposed within the shield and defining binding surfaces that form an aperture configured for slidable receipt of the inner needle between the retracted position and the extended position,
   the binding member including at least one drag inducing member such that the at least one drag inducing member engages the inner needle during slidable receipt of the inner needle to create a drag force with the inner needle, the drag force and shield facilitating rotation of the binding member relative to a longitudinal axis of the inner needle such that the binding surfaces engage the inner needle to prevent slidable movement of the inner needle in the extended position of the shield,
   the binding member further including a needle communicating surface extending therefrom such that the needle communicating surface is engageable with the inner needle to prevent rotation of the binding member,
   a retainer for releasable engagement with the needle hub, and
   the binding member further including a binding member reset surface aligned with a hub reset surface.

2. A medical needle shield apparatus as recited in claim 1, wherein the at least one drag inducing member defines a cavity that is substantially aligned with the aperture, the cavity being configured for slidable receipt of the needle to create the drag force with the needle.

3. A medical needle shield apparatus as recited in claim 1, wherein the binding member includes a substantially planar aperture plate that includes the binding surfaces that form the aperture.

4. A medical needle shield apparatus as recited in claim 3, wherein the at least one drag inducing member includes a pair of arms extending from the aperture plate.

5. A medical needle shield apparatus as recited in claim 4, wherein said pair of arms includes a deflectable member.

6. A medical needle shield apparatus as recited in claim 1, wherein the binding member is rotatable, relative to a longitudinal axis of the inner needle, between a non-binding orientation whereby the inner needle is slidable relative to the binding member and a binding orientation whereby the binding surfaces engage the inner needle to prevent slidable movement of the inner needle in the extended position of the at least one shield.

7. A medical needle shield apparatus as recited in claim 1, wherein the shield includes a housing that defines at least one blocking member extending from an interior surface thereof, the at least one blocking member being engageable with the binding member for urging the binding member to a binding orientation.

8. A medical needle shield apparatus as recited in claim 3, wherein the shield includes a housing that defines at least one blocking member extending from an interior surface thereof, the aperture plate being axially movable for engagement with the at least one blocking member that causes rotation of the binding member to a binding orientation.

9. A medical needle shield apparatus as recited in claim 1, wherein the at least one shield is supported for relative rotational movement by at least one bearing.

10. A medical needle shield apparatus as recited in claim 1, wherein the inner needle is attached to a handle for manipulation thereof.

11. A medical needle shield apparatus as recited in claim 1, wherein the needle hub is releasably mountable with a housing of the at least one shield.

12. A medical needle shield apparatus as recited in claim 1, wherein the needle hub defines a hub slot that is configured to receive the retainer of the binding member.

13. A medical needle shield apparatus as recited in claim 1, wherein the binding member includes at least one outwardly arcuate arm that extends to the needle communicating surface.

14. A medical needle shield apparatus as recited in claim 1, further comprising a second shield for enclosing the distal end of the outer needle.

15. A medical needle shield apparatus as recited in claim 1, wherein said binding member reset surface comprises the distal facing surface of said retainer.

16. A medical needle shield apparatus as recited in claim 1, wherein said hub reset surface is configured to deflect said binding member reset surface to facilitate rotation of the binding member relative to said longitudinal axis such that said binding surface disengages the inner needle.

17. A medical needle shield according to claim 1, wherein said medical needle is adapted for bone biopsy.

18. A medical needle shield according to claim 1, wherein said medical needle is adapted for catheter introduction to a patient.

19. A medical needle shield apparatus as recited in claim 1, wherein said hub reset surface is separate from said hub and urged by a spring toward said binding member reset surface.

20. A medical needle shield apparatus of claim 19, further comprising a luer male taper configured with said hub.

21. A medical needle shield according to claim 1, wherein said medical needle operates in communication with a port access device.

22. A medical needle shield according to claim 1, further comprising a protective needle sheath member.

23. A medical needle shield apparatus comprising:
a needle hub having an outer needle cannula extending therefrom, an inner needle being disposed for slidable movement with the outer needle cannula; and
a shield being extensible from a retracted position to an extended position to enclose a distal end of the outer needle cannula,
the shield including a binding member disposed within the shield and defining binding surfaces that form an aperture configured for slidable receipt of the outer needle cannula between the retracted position and the extended position,
the binding member including at least one drag inducing member such that the at least one drag inducing member engages the outer needle cannula during slidable receipt of the outer needle cannula to create a drag force with the outer needle cannula, the drag force and shield facilitating rotation of the binding member relative to a longitudinal axis of the outer needle cannula such that the binding surfaces engage the outer needle cannula to prevent slidable movement of the outer needle cannula in the extended position of the shield, and
the binding member further including a needle communicating surface extending therefrom such that the needle communicating surface is engageable with the outer needle cannula to prevent rotation of the binding member.

24. A medical needle shield apparatus as recited in claim 23, wherein the binding member is rotatable, relative to a longitudinal axis of the outer needle cannula, between a non-binding orientation whereby the outer needle cannula is slidable relative to the binding member and a binding orientation whereby the binding surfaces engage the outer needle cannula to prevent slidable movement of the outer needle cannula in the extended position of the shield.

25. A medical needle shield apparatus as recited in claim 23, wherein the shield includes a housing that defines at least one blocking member extending from an interior surface thereof, the binding member including an aperture plate being axially movable for engagement with the at least one blocking member that causes rotation of the binding member to a binding orientation.

26. A medical needle shield apparatus as recited in claim 23, wherein the shield includes a funnel portion adapted for use as a probe guide at a distal end thereof configured for receipt of a probe, the probe being configured for slidable movement with the outer needle cannula.

27. A medical needle shield apparatus comprising:
a needle hub having an outer needle cannula extending therefrom to a distal end, an inner needle being disposed for slidable movement with the outer needle cannula, a handle being attached to the inner needle; and
a shield being releasably mountable to the needle hub and extensible from a retracted position to an extended position to enclose a distal end of the inner needle, the handle being disposed adjacent the shield,
the shield including a binding member disposed within the shield and defining binding surfaces that form an aperture configured for slidable receipt of the inner needle between the retracted position and the extended position,
the binding member including at least one drag inducing member such that the at least one drag inducing member engages the inner needle during slidable receipt of the inner needle to create a drag force with the inner needle, the drag force and shield facilitating rotation of the binding member relative to a longitudinal axis of the inner needle such that the binding surfaces engage the inner needle to prevent slidable movement of the inner needle in the extended position of the shield, and
the binding member further including a needle communicating surface extending therefrom such that the needle communicating surface is engageable with the inner needle to prevent rotation of the binding member, a retainer for releasable engagement with a hub slot of the needle hub, and a binding member reset surface aligned for engagement with a hub reset surface.

28. A medical needle shield apparatus as recited in claim 27, wherein the binding member is rotatable, relative to a longitudinal axis of the inner needle, between a non-binding orientation whereby the inner needle is slidable relative to the binding member and a binding orientation whereby the binding surfaces engage the inner needle to prevent slidable movement of the inner needle in the extended position of the shield.

29. A medical needle shield apparatus as recited in claim 27, wherein the shield includes a housing that defines at least one blocking member extending from an interior surface thereof, the binding member including an aperture plate being axially movable for engagement with the at least one blocking member that causes rotation of the binding member to a binding orientation.

30. A medical needle shield apparatus as recited in claim 27, further comprising a luer slip or luer lock attachment feature.

31. A medical needle shield apparatus as recited in claim 27, further comprising a flash chamber in communication with the inner needle, the flash chamber having a fitting that facilitates connection to a medical device.

32. A medical needle shield apparatus as recited in claim 27, further comprising
an adjustable depth stop device for setting desired needle insertion depth, said depth stop device slidably disposed on the needle cannula and said at least one shield being substantially disposed within said depth stop device.

33. A medical needle shield apparatus comprising:
a needle hub having an outer needle cannula extending therefrom to a distal end, an inner needle being disposed for slidable movement with the outer needle cannula; and
at least one shield being extensible from a retracted position to an extended position to enclose a distal end of the inner needle,
the needle shield further including a reset surface aligned with a hub reset surface for engagement therewith to allow reuse of the shield in a shielded configuration.

* * * * *